United States Patent
Ladouceur et al.

(10) Patent No.: US 6,780,859 B2
(45) Date of Patent: Aug. 24, 2004

(54) BENZOFURAN AND DIHYDROBENZOFURAN DERIVATIVES USEFUL AS BETA-3 ADRENORECEPTOR AGONISTS

(75) Inventors: Gaetan H. Ladouceur, Branford, CT (US); William R. Schoen, Madison, CT (US); Michael J. Burke, West Haven, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 296 days.

(21) Appl. No.: 10/241,250

(22) Filed: Sep. 10, 2002

(65) Prior Publication Data

US 2003/0195352 A1 Oct. 16, 2003

Related U.S. Application Data

(60) Provisional application No. 60/318,882, filed on Sep. 14, 2001.

(51) Int. Cl.$^7$ .................. A61K 31/65; A61K 31/42; C07D 417/02; C07D 413/02; C07D 47/02
(52) U.S. Cl. ............... 514/233.5; 514/252.13; 514/337; 514/365; 544/153; 544/376; 546/196; 548/202; 548/215; 548/311.4; 549/467
(58) Field of Search .............. 549/467; 548/202, 548/215; 546/196; 544/153, 376; 514/252.13, 33

(56) References Cited

U.S. PATENT DOCUMENTS

| | | | |
|---|---|---|---|
| 3,706,764 A | 12/1972 | Nakanishi et al. | 260/327 |
| 3,803,176 A | 4/1974 | Christensen et al. | 260/345.2 |
| 4,647,579 A | 3/1987 | Kabbe et al. | 514/456 |
| 4,650,812 A | 3/1987 | Cohen et al. | 514/456 |
| 4,654,362 A | 3/1987 | Van Lommen et al. | 514/452 |
| 5,393,775 A | 2/1995 | Le Baut et al. | 514/456 |
| 5,451,677 A | 9/1995 | Fisher et al. | 546/138 |
| 5,516,917 A | 5/1996 | Djuric et al. | 548/525 |
| 5,541,197 A | 7/1996 | Fisher et al. | 514/311 |
| 5,561,142 A | 10/1996 | Fisher et al. | 514/312 |
| 5,663,194 A | 9/1997 | Mewshaw | 514/456 |
| 5,977,154 A | 11/1999 | Bell et al. | 514/394 |
| 6,051,586 A | 4/2000 | Ladouceur et al. | 514/337 |

FOREIGN PATENT DOCUMENTS

| | | | |
|---|---|---|---|
| EP | 0801060 | 10/1997 | ......... C07D/209/42 |
| FR | 2746395 | 7/1999 | |
| JP | 8165276 | 6/1996 | |
| WO | 9735835 | 2/1997 | ......... C07C/217/74 |
| WO | 9746556 | 12/1997 | ......... C07D/413/10 |
| WO | 9832733 | 7/1998 | ......... C07D/417/12 |
| WO | 9965877 | 12/1999 | ......... C07D/213/80 |
| WO | 0206258 | 1/2000 | |

*Primary Examiner*—T. Solola
(74) *Attorney, Agent, or Firm*—Susan M. Pellegrino

(57) ABSTRACT

This invention relates to novel benzofuran and dihydrobenzofuran compounds, pharmaceutical compositions containing such compounds, and methods of treating beta-3 adrenoreceptor-mediated conditions with such compositions.

16 Claims, No Drawings

BENZOFURAN AND DIHYDROBENZOFURAN DERIVATIVES USEFUL AS BETA-3 ADRENORECEPTOR AGONISTS

This application claims benefit of U.S. Provisional Application Serial No. 60/318,882, filed Sep. 14, 2001, the contents of which are incorporated herein by reference in their entirety.

FIELD OF THE INVENTION

This invention relates to novel benzofuran and dihydrobenzofuran compounds, pharmaceutical compositions containing such compounds, and methods of treating beta-3 adrenoreceptor-mediated conditions with such compositions.

BACKGROUND OF THE INVENTION

Adrenoreceptors, or adrenergic receptors, are sites on effector organs that are innervated by postganglionic adrenergic fibers of the sympathetic nervous system, and are classified as either alpha-adrenergic or beta-adrenergic receptors. Alpha-adrenergic receptors respond to norepinephrine and to such blocking agents as phenoxybenzamine and phentolamine, whereas beta-adrenergic receptors respond to epinephrine and to such blocking agents as propranolol.

Beta-adrenergic receptors are sub-classified as beta-1, beta-2, and beta-3 adrenoreceptors. Generally, beta-1 stimulation causes cardiostimulation, whereas beta-2 stimulation causes bronchodilation and vasodilation.

Beta-3 receptors are found on the cell surface of both white and brown adipocytes where their stimulation promotes both lipolysis and energy expenditure. Agonists of beta-3 adrenoreceptors are known to be useful in the treatment of hyperglycemia (diabetes) and obesity in mammals, as well as in the treatment of gastrointestinal disorders and neurogenetic inflammation (U.S. Pat. No. 5,561,142). Additionally, they are known to lower triglyceride and cholesterol levels and to raise high-density lipoprotein (HDL) levels in mammals (U.S. Pat. No. 5,451,677). Accordingly, they are useful in the treatment of conditions such as hypertriglyceridemia, hypercholesterolemia and low HDL levels as well as in the treatment of atherosclerotic and cardiovascular diseases and related conditions. Agonists of beta-3 adrenoreceptors are also useful in treating patients with Syndrome X, impaired fasting glucose, and/or impaired glucose tolerance.

Additionally, the compounds of this invention are effective in the treatment of ocular hypertension and glaucoma, and in the treatment of urinary disorders including pollakiuria and incontinence, as well as in the treatment of prostate disease and as topical anti-inflammatory agents.

It has now been found that certain novel benzofuran and dihydrobenzofuran derivatives are effective as beta-3 adrenoreceptor agonists and are useful in the treatment of beta-3 adrenoreceptor-mediated conditions.

DESCRIPTION OF THE INVENTION

The invention specifically relates to benzofuran compounds of Formula I:

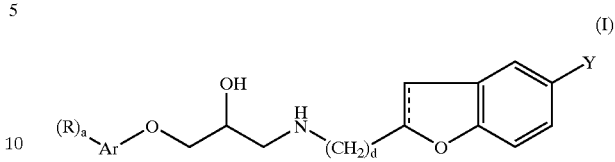

(I)

wherein:

--- represents a single or double bond;

R is hydroxy, oxo, halo, cyano, nitro, $C_1$–$C_{10}$ alkyl, $C_1$–$C_{10}$ haloalkyl, $CF_3$, $NR^1R^1$, $SR^1$, $OR^1$, $SO_2R^2$, $OCOR^2$, $NR^1COR^2$, $COR^2$, $NR^1SO_2R^2$, phenyl, or a 5- or 6-membered heterocyclic ring with from 1 to 4 heteroatoms selected from O, S, and N, each cyclic moiety being optionally substituted with one or more substituents independently selected from hydroxy, $R^1$, halo, cyano, $NR^1R^1$, $SR^1$, $CF_3$, $OR^1$, $C_3$–$C_8$ cycloalkyl, $NR^1COR^2$, $COR^2$, $SO_2R^2$, $OCOR^2$, $NR^1SO_2R^2$, $C_1$–$C_{10}$ alkyl, and $C_1$–$C_{10}$ alkoxy;

$R^1$ is hydrogen or $C_1$–$C_{10}$ alkyl optionally substituted with 1 to 4 substituents each independently selected from hydroxy, halo, $CO_2H$, $CO_2(C_1$–$C_{10}$ alkyl), $C_1$–$C_{10}$ alkoxy, and phenyl optionally substituted with $CO_2H$, $CO_2(C_1$–$C_{10}$ alkyl) or $C_1$–$C_{10}$ alkyl; or $C_3$–$C_8$ cycloalkyl, phenyl or naphthyl, each optionally substituted with 1 to 4 substituents, and each independently selected from halo, nitro, oxo, $C_1$–$C_{10}$ alkyl, $C_1$–$C_{10}$ alkoxy, and $C_1$–$C_{10}$ alkylthio;

$R^2$ is $R^1$, $OR^1$, $NR^1R^1$ or a 5- or 6-membered heterocyclic ring with one or more heteroatoms selected from O, S, and N, said heterocyclic ring being optionally substituted with $R^1$;

Ar is phenyl optionally fused to a 5- or 6-membered heterocyclic ring containing 1 to 4 heteroatoms each independently selected from O, S, and N, wherein the heterocyclic ring in turn is optionally fused to another phenyl ring; or a 5- or 6-membered heterocyclic ring containing 1 to 4 heteroatoms each independently selected from N, S, and O, optionally fused to a phenyl ring;

Y is $C_1$–$C_{10}$ alkyl optionally substituted with 1 to 4 substituents each independently selected from hydroxy, halo, $CO_2H$, $CO_2(C_1$–$C_{10}$ alkyl), $C_1$–$C_{10}$ alkoxy, $C_1$–$C_{10}$ alkylthio, and phenyl optionally substituted with $CO_2H$, $CO_2(C_1$–$C_{10}$alkyl), or $C_1$–$C_{10}$ alkyl; or phenyl optionally fused to another phenyl ring or to a 5- or 6-membered heterocyclic ring containing 1 to 4 heteroatoms selected from N, S, and O; or a 5- or 6-membered heterocyclic ring containing one or more heteroatoms selected from N, S, and O, optionally fused to a phenyl ring;

each cyclic moiety being optionally substituted with one or more substituents independently selected from $COR^2$, halo, $NO_2$, $OR^1$, $R^1$, $SR^1$, $NR^1R^1$, $(C_1$–$C_{10}$ alkyl) $OR^2$, phenyl or tetrazolo;

a is 0, 1, 2, 3, 4, or 5; and d is 1 or 2;

and pharmaceutically acceptable salts and esters thereof.

The terms identified above have the following meaning throughout:

$C_1$–$C_{10}$ alkyl means straight or branched chain alkyl groups having from one to about ten carbon atoms, which may be saturated, unsaturated, or partially saturated. Such groups include methyl, ethyl, n-propyl, isopropyl, n-butyl, isobutyl, sec-butyl, tert-butyl, as well as vinyl, allyl, propynyl, butenyl, butadienyl, isopropenyl, methyleneyl, ethylenyl, propenyl, ethynyl, and the like.

$C_1$–$C_{10}$ haloalkyl means straight or branched chain alkyl groups having from one to about ten carbon atoms where any C—C bond may be saturated or unsaturated, the alkyl groups being substituted at any available carbon atom with one or more halogen atoms. Such groups include trifluoromethyl, trichloromethyl, pentafluoroethyl, fluoromethyl, fluoroethylenyl, 6-chlorohexyl, and the like.

The term $C_1$–$C_{10}$ alkoxy means $C_1$–$C_{10}$ alkyl radicals as defined above bonded through an oxygen (—O—) linkage. Such groups include methoxy, ethoxy, n-propoxy, isopropoxy, n-butoxy, isobutoxy, sec-butoxy, tert-butoxy, and the like.

The term $C_1$–$C_{10}$ alkylthio means $C_1$–$C_{10}$ alkyl radicals as defined above bonded through a sulfur (—S—) linkage. Such groups include methylthio, ethylthio, n-propylthio, isopropylthio, n-butylthio, isobutylthio, sec-butylthio, tert-butylthio, and the like.

$C_3$–$C_8$ cycloalkyl means saturated mono cyclic alkyl groups of from 3 to about 8 carbon atoms. Such groups include cyclopropyl, cyclopentyl, cyclohexyl, and the like.

Halo includes fluoro, chloro, bromo, and iodo, unless specifically stated otherwise.

Each of $R^2$, Ar, and Y includes any 5- or 6-membered saturated or unsaturated heterocyclic group having any combination of one or more N, S, or O atoms, with the point of attachment being at any available position on the heterocyclic ring. Where there is more than one heteroatom in a single cyclic group, each heteroatom may be chosen independently of any other heteroatom, in each occurrence. These moieties include, but are not limited to, such 5-membered heterocylic groups as furyl, thienyl, pyrrolyl, oxazolyl, thiazolyl, imidazolyl, pyrazolyl, isoxazolyl, isothiazolyl, tetrahydrofuryl, dihydrofuryl, pyrrolidinyl, pyrrolinyl, dihydrothienyl, tetrahydrothienyl, dioxolyl, oxazolinyl, oxazolidinyl, isoxazolinyl, isoxazolidinyl, thiazolinyl, thiazolidinyl, isothiazolinyl, isothiazolidinyl, imidazolinyl, imidazolidinyl, pyrazolinyl, pyrazolidinyl, triazolyl, triazolinyl, triazolidinyl, oxadiazolyl, thiadiazolyl, furazanyl, tetrazolyl, and the like. Such moieties also include, but are not limited to, such 6-membered heterocyclic rings such as pyridyl, pyrimidinyl, pyrazinyl, pyridazinyl, pyranyl, dihydropyranyl, thiopyranyl, triazinyl, dioxanyl, piperidinyl, piperazinyl, pyrazinyl, morpholinyl, and the like.

Each of Ar and Y also includes phenyl fused to any 5- or 6-membered heterocyclic ring described above to form a bicyclic moiety, which may be saturated or unsaturated and may have any combination of one or more N, S, or O atoms, with the point of attachment being any at available position on the phenyl ring. These moieties include, but are not limited to, such phenyl fused 5-membered heterocyclic groups as benzofuryl, dihydrobenzofuryl, benzothienyl, dihydrobenzothienyl, indolyl, indazolyl, indolinyl, indazolinyl, benzoxazolyl, benzoxazolinyl, benzothiazolyl, benzothiazolinyl, benzimidazolyl, benzimidazolinyl, benzisoxazolyl, benzisoxazolinyl, benzothiadiazolyl, benzisothiazolyl, benzisothiazolinyl, benzotriazolyl, benzoxadiazolyl, benzoxadiazolinyl, benzothiadiazolyl, benzopyrazolinyl, and the like. Such moieties also include, but are not limited to, such phenyl fused 6-membered heterocyclic groups as quinolyl, isoquinolyl, quinazolinyl, quinoxalinyl, cinnolinyl, chromenyl, phthalazinyl, dihydrobenzopyranyl, benzothiopyranyl, dihydrobenzothiopyranyl, benzoxazinyl, benzodioxanyl, benzodioxenyl, and the like.

Ar also includes phenyl fused to any 5- or 6-membered heterocyclic ring to form a bicyclic moiety as described above, which is further fused on the heterocyclic ring to a second phenyl ring, forming a tricyclic system, with the point of attachment to the core structure of the compound of Formula I being at any available position of the first phenyl ring. These include, but are not limited to, such groups as carbazolyl, carbazolinyl, acridinyl, xanthenyl, phenoxathiinyl, phenoxazinyl, phenanthridinyl, dibenzofuryl, dibenzopyranyl, dibenzodioxanoyl, phenazinyl, thianthrenyl and the like.

Ar also includes any 5 or 6-membered saturated or unsaturated heterocyclic ring having any combination of one or more N, S, or O atoms, which is further fused to a phenyl ring, with the point of attachment to the core molecule of Formula I being at any available position on the heterocyclic ring. These include, but are not limited to, such phenyl-fused with 5-membered hetero-bicyclic moieties as benzofuryl, dihydrobenzofuryl, benzothienyl, dihydrobenzothienyl, indoyl, indazolyl, indolizinyl, indolinyl, indazolinyl, benzoxazolyl, benzoxazolinyl, benzothiazolyl, benzothiazolinyl, benzimidazolyl, benzimidazolinyl, benzisoxazolyl, benzisoxazolinyl, benzisothiazolyl, benzoisothiazolinyl, benzopyrazolinyl, and the like. It also includes such phenyl-fused with 6-membered hetero-bicyclic groups as quinolyl, isoquinolyl, quinazolinyl, quinoxalinyl, cinnolinyl, chromenyl, phthalazinyl, dihydrobenzopyranyl, benzothiopyranyl, dihydrobenzothiopyranyl, benzoxazinyl, benzodioxanyl, benzodioxenyl, and the like.

When any moiety is described as being substituted, it may have one or more of the indicated substituents that may be located at any available position on the moiety. When there are two or more substituents on any moiety, each term may be defined independently of any other in each occurrence. For example, $NR^1R^1$ may represent $NH_2$, $NHCH_3$, $N(CH_3)CH_2CH_2CH_3$, and the like.

Examples of the compound of Formula I, which are illustrative of the present invention, but not limiting in any way, are listed in Table 1.

TABLE 1
Illustrative Examples of the Invention
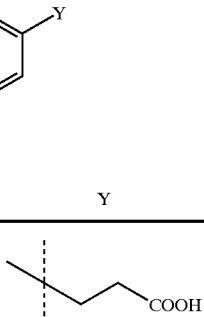
| Example No. | R | a | Ar | d | Y |
|---|---|---|---|---|---|
| 1 | — | 0 | Ph | 1 | 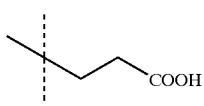COOH |
| 2 | 3-CONH-i-Bu | 1 | Ph | 1 | COOH |
| 3 | 2,4-diMe-6-Cl | 3 | Ph | 1 | COOH |
| 4 | 2,3,5,6-tetra-Cl | 4 | Ph | 1 | COOH |
| 5 | 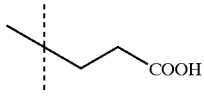 4- | 1 | Ph | 1 | COOH |
| 6 | 2-Cl | 1 | Ph | 1 | COOH |
| 7 | 2-CN | 1 | 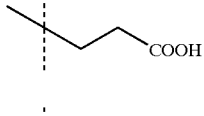 | 1 | COOH |
| 8 | — | 0 | Ph | 1 | 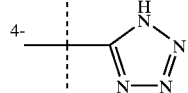COOH |
| 9 | — | 0 | Ph | 1 | 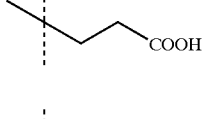COOH, SMe |
| 10 | — | 0 | Ph | 1 | 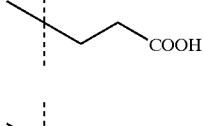COOMe |
| 11 | — | 0 | Ph | 1 | —Et |
| 12 | — | 0 | Ph | 1 | —CF₃ |
| 13 | — | 0 | Ph | 1 | -t-Bu |

TABLE 1-continued
Illustrative Examples of the Invention
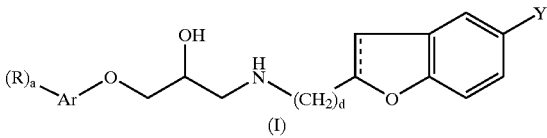
(I)
| Example No. | R | a | Ar | d | Y |
|---|---|---|---|---|---|
| 14 | — | 0 | Ph | 2 | 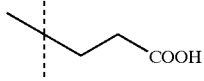 |
| 15 | 2,4-diCl | 2 | Ph | 1 | 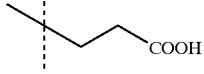 |
| 16 | 2,3,4,5,6-penta-F | 5 | Ph | 1 | 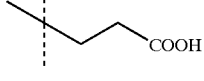 |
| 17 | 3-NO$_2$ | 1 | Ph | 1 | 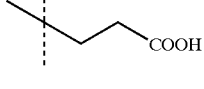 |
| 18 | 2-F-6-MeO | 2 | Ph | 1 | 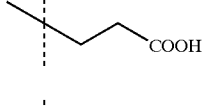 |
| 19 | 2-Ph | 1 | Ph | 1 | 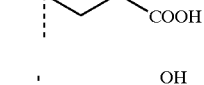 |
| 20 | 3-CF$_3$ | 1 | Ph | 1 |  |
| 21 | 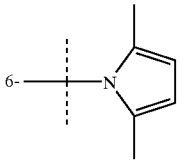 | 1 | 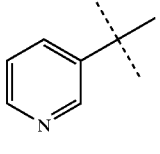 | 1 | 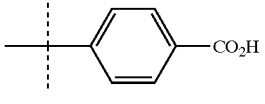 |
| 22 | 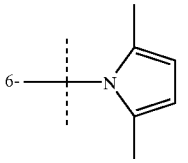 | 1 | 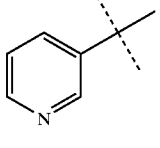 | 2 | 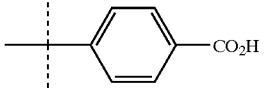 |
| 23 | — | 0 | 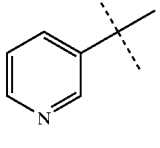 | 1 | 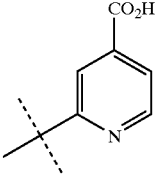 |

TABLE 1-continued
Illustrative Examples of the Invention
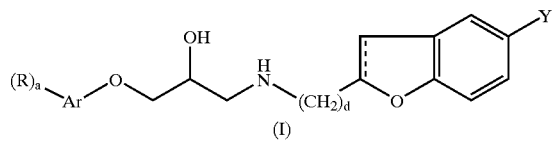
(I)
| Example No. | R | a | Ar | d | Y |
|---|---|---|---|---|---|
| 24 | — | 0 | Ph | 1 | pyridine-4-CO₂H (2-linked) |
| 25 | — | 0 | 3-pyridyl | 1 | pyridine-3-CO₂H (5-linked) |
| 26 | — | 0 | 3-pyridyl | 1 | pyridine-3-CO₂H (2-linked) |
| 27 | — | 0 | 3-pyridyl | 1 | pyridine-3-CONH₂ (6-linked) |
| 28 | — | 0 | 3-pyridyl | 1 | 4-methylpiperazine (NH) |
| 29 | — | 0 | 3-pyridyl | 1 | 2-thienyl |
| 30 | — | 0 | 3-pyridyl | 1 | 5-CO₂H-2-thienyl |
| 31 | — | 0 | 3-pyridyl | 1 | 3-thienyl |

TABLE 1-continued
Illustrative Examples of the Invention
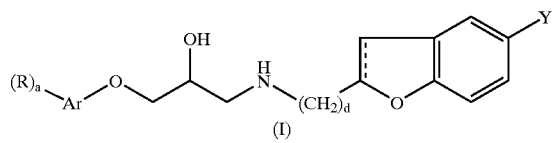
(I)
| Example No. | R | a | Ar | d | Y |
|---|---|---|---|---|---|
| 32 | — | 0 | 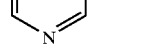 | 1 |  |
| 33 | — | 0 | 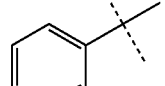 | 1 | 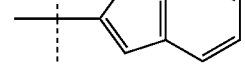 |
| 34 | — | 0 |  | 1 | 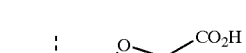 |
| 35 | — | 0 | 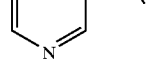 | 1 | 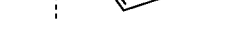 |
| 36 | — | 0 | 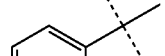 | 1 | 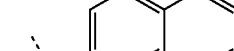 |
| 37 | — | 0 | 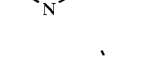 | 1 |  |
| 38 | — | 0 | 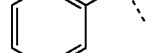 | 1 | 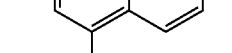 |
| 39 | — | 0 |  | 1 | 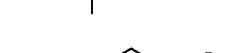 |

TABLE 1-continued
Illustrative Examples of the Invention
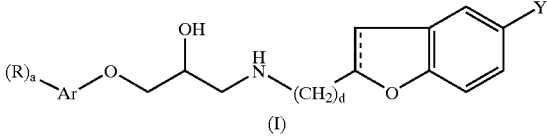
(I)
| Example No. | R | a | Ar | d | Y |
|---|---|---|---|---|---|
| 40 | — | 0 | 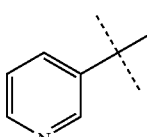 | 1 | 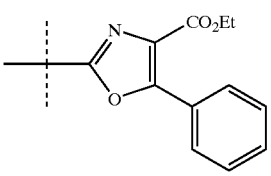 |
| 41 | — | 0 | 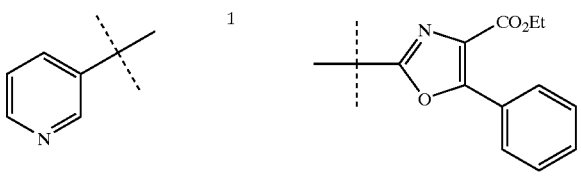 | 1 | 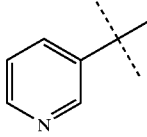 |
| 42 | — | 0 | 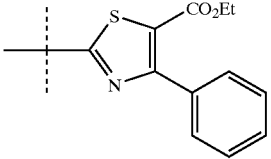 | 1 | 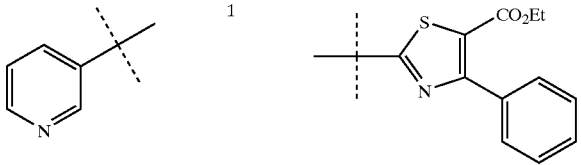 |
| 43 | — | 0 | Ph | 1 | 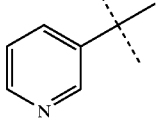 |
| 44 | — | 0 | Ph | 2 | 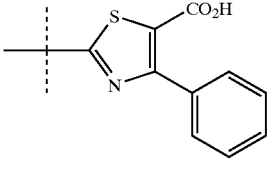 |
| 45 | 6-$NH_2$ | 1 |  | 1 | 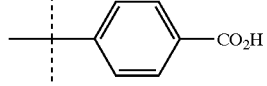 |
| 46 | 6-$NH_2$ | 1 | 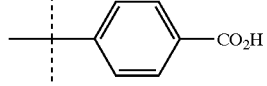 | 2 | 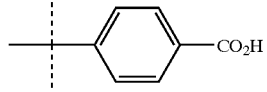 |
| 47 | — | 0 | 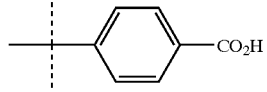 | 1 | 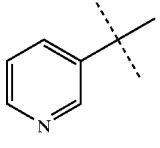 |

TABLE 1-continued
Illustrative Examples of the Invention
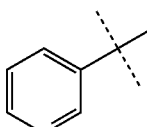
(I)
| Example No. | R | a | Ar | d | Y |
|---|---|---|---|---|---|
| 48 | — | 0 | 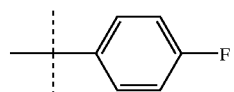 | 1 | 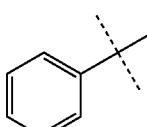 |
| 49 | — | 0 | 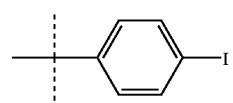 | 1 | 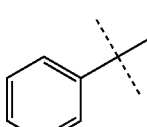 |
| 50 | — | 0 | 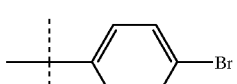 | 1 | 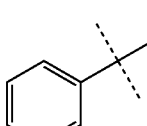 |
| 51 | — | 0 | 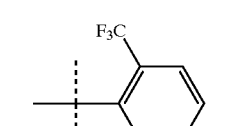 | 1 | 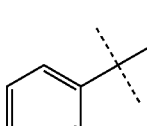 |
| 52 | — | 0 | 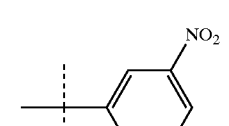 | 1 | 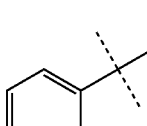 |
| 53 | — | 0 | 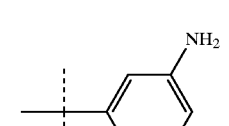 | 1 | 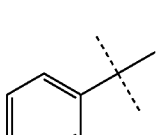 |
| 54 | — | 0 | 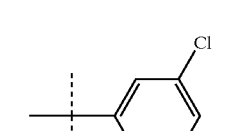 | 1 | 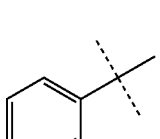 |
| 55 | — | 0 | 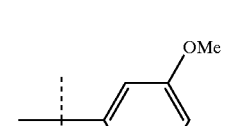 | 1 |  |

TABLE 1-continued
Illustrative Examples of the Invention
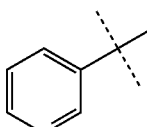
(I)
| Example No. | R | a | Ar | d | Y |
|---|---|---|---|---|---|
| 56 | — | 0 | 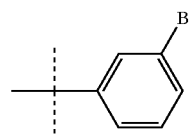 | 1 | 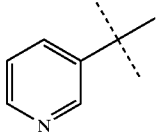 |
| 57 | — | 0 | 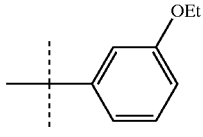 | 1 | 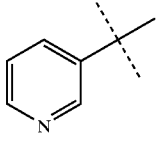 |
| 58 | — | 0 | 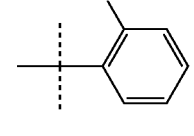 | 1 | 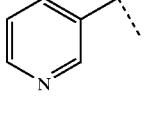 |
| 59 | — | 0 | 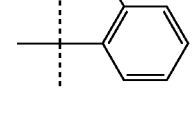 | 1 | 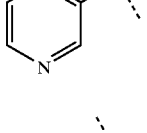 |
| 60 | — | 0 | 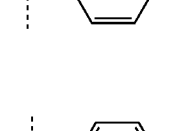 | 1 | 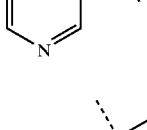 |
| 61 | — | 0 |  | 1 | 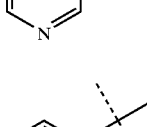 |
| 62 | — | 0 |  | 1 | 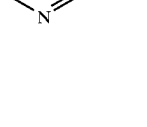 |
| 63 | — | 0 |  | 1 | |

TABLE 1-continued
Illustrative Examples of the Invention
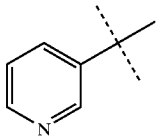
(I)
| Example No. | R | a | Ar | d | Y |
|---|---|---|---|---|---|
| 64 | — | 0 | 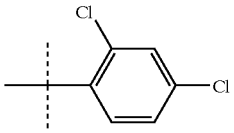 | 1 | 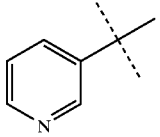 |
| 65 | — | 0 | 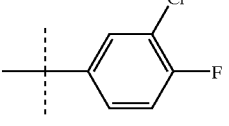 | 1 | 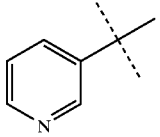 |
| 66 | — | 0 | 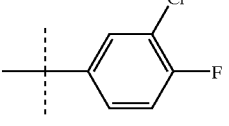 | 1 | 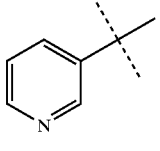 |
| 67 | — | 0 | 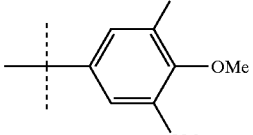 | 1 | 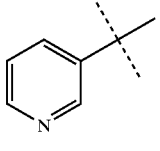 |
| 68 | — | 0 | 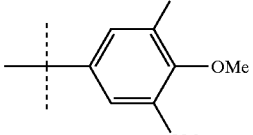 | 1 | 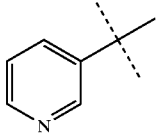 |
| 69 | — | 0 | 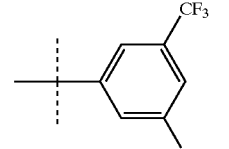 | 1 | 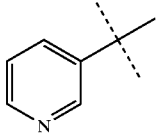 |
| 70 | — | 0 | 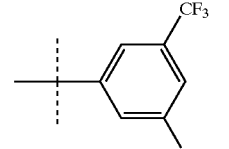 | 1 | 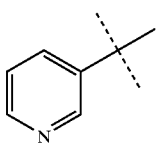 |

TABLE 1-continued
Illustrative Examples of the Invention
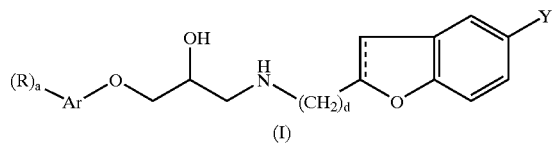
(I)
| Example No. | R | a | Ar | d | Y |
|---|---|---|---|---|---|
| 71 | — | 0 | 3-pyridyl | 1 | 9-phenanthryl |
| 72 | — | 0 | 3-pyridyl | 1 | 4-(1H-tetrazol-5-yl)phenyl |
| 73 | — | 0 | 3-pyridyl | 2 | 4-(1H-tetrazol-5-yl)phenyl |
| 74 | — | 0 | 3-pyridyl | 1 | 4-(1H-tetrazol-5-yl)phenyl |
| 75 | — | 0 | 3-pyridyl | 1 | 4-$CO_2Me$-phenyl |
| 76 | — | 1 | 3-pyridyl | 1 | 4-$CO_2Me$-phenyl |
| 77 | — | 0 | Ph | 1 | 4-$CO_2Me$-phenyl |
| 78 | — | 0 | 3-pyridyl | 1 | 4-$CO_2Me$-phenyl |

TABLE 1-continued

Illustrative Examples of the Invention (I)

| Example No. | R | a | Ar | d | Y |
|---|---|---|---|---|---|
| 79 | — | 0 | 3-pyridyl | 1 | 4-(CH₂CO₂H)-phenyl |
| 80 | — | 0 | 3-pyridyl | 1 | 4-(C(O)NH₂)-phenyl |
| 81 | — | 0 | 3-pyridyl | 1 | 4-(C(O)N(Et)₂)-phenyl |
| 82 | — | 0 | 3-pyridyl | 1 | 4-(C(O)NH-i-Bu)-phenyl |
| 83 | — | 0 | 3-pyridyl | 1 | 4-(C(O)NHPh)-phenyl |
| 84 | — | 0 | 3-pyridyl | 1 | 4-(C(O)NHMe)-phenyl |
| 85 | — | 0 | 3-pyridyl | 1 | 4-(C(O)NHEt)-phenyl |
| 86 | — | 0 | 3-pyridyl | 1 | 4-(C(O)NH-t-Bu)-phenyl |

TABLE 1-continued
Illustrative Examples of the Invention
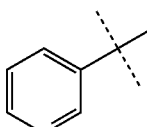
(I)
| Example No. | R | a | Ar | d | Y |
|---|---|---|---|---|---|
| 87 | — | 0 | 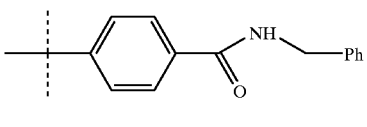 | 1 | 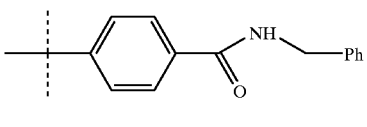 |
| 88 | — | 0 | 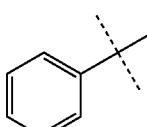 | 1 | 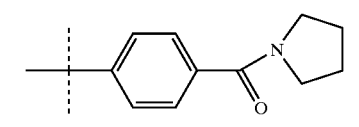 |
| 89 | — | 0 | 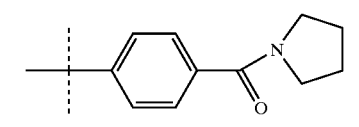 | 1 | 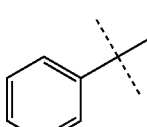 |
| 90 | — | 0 | 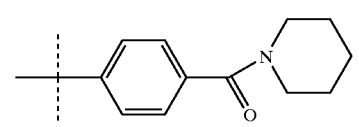 | 1 | 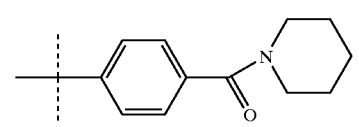 |
| 91 | — | 0 | 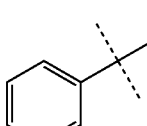 | 1 | 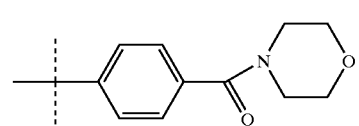 |
| 92 | — | 0 | 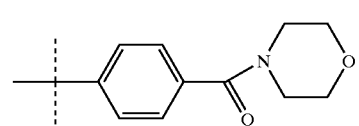 | 1 | 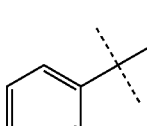 |
| 93 | — | 0 | 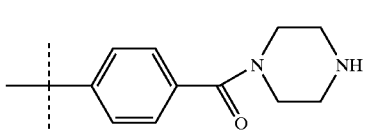 | 1 | 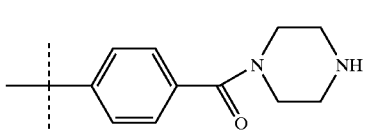 |
| 94 | — | 0 | 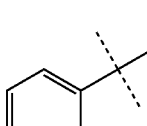 | 1 | 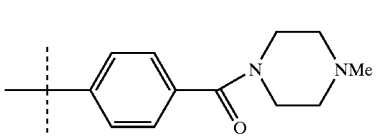 |

TABLE 1-continued
Illustrative Examples of the Invention
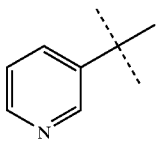
(I)
| Example No. | R | a | Ar | d | Y |
|---|---|---|---|---|---|
| 95 | — | 0 | 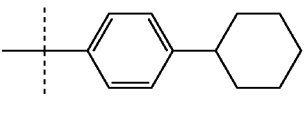 | 1 | 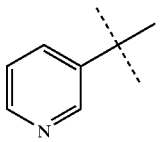 |
| 96 | — | 0 | 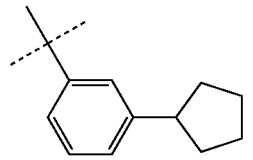 | 1 | 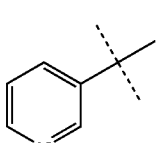 |
| 97 | — | 0 | 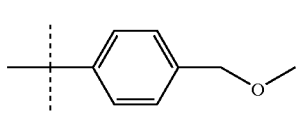 | 1 | 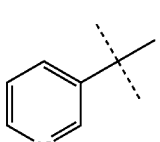 |
| 98 | — | 0 | 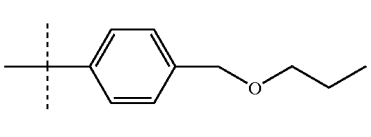 | 1 | 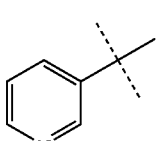 |
| 99 | 4-OH | 1 | 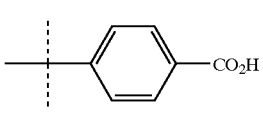 | 1 | 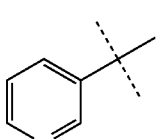 |
| 100 | 6-OH | 1 | 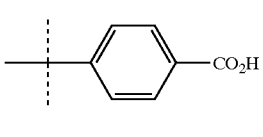 | 1 | 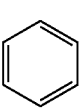 |
| 101 | 4-CN | 1 | 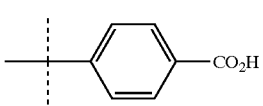 | 1 | 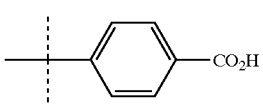 |
| 102 | 2-Me | 1 | Ph | 1 | 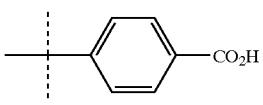 |
| 103 | 3-Et | 1 | Ph | 1 | |

TABLE 1-continued

Illustrative Examples of the Invention $(R)_a-Ar-O-CH_2-CH(OH)-CH_2-NH-(CH_2)_d-\text{[benzofuran-2-yl]}-Y$ (I)

| Example No. | R | a | Ar | d | Y |
|---|---|---|---|---|---|
| 104 | 3-CF₃ | 1 | Ph | 1 | -C₆H₄-CO₂H (para) |
| 105 | 3-NH₂ | 1 | Ph | 1 | -C₆H₄-CO₂H (para) |
| 106 | 3-NH—Me | 1 | Ph | 1 | -C₆H₄-CO₂H (para) |
| 107 | 3-N(Et)₂ | 1 | Ph | 1 | -C₆H₄-CO₂H (para) |
| 108 | 4-OMe | 1 | Ph | 1 | -C₆H₄-CO₂H (para) |
| 109 | 2,3,5,6-tetra-Cl | 4 | Ph | 1 | -C₆H₄-CO₂H (para) |
| 110 | 4-OEt | 1 | Ph | 1 | -C₆H₄-CO₂H (para) |
| 111 | 4-O-cyc-Pr | 1 | Ph | 1 | -C₆H₄-CO₂H (para) |
| 112 | 2,3,4,5,6-penta-F | 5 | Ph | 1 | -C₆H₄-CO₂H (para) |
| 113 | 2,4-di-Cl | 2 | Ph | 1 | -C₆H₄-CO₂H (para) |
| 114 | 2,4-di-Me | 2 | Ph | 1 | -C₆H₄-CO₂H (para) |
| 115 | 2,4-di-Cl | 2 | Ph | 1 | -C₆H₄-CO₂H (para) |

TABLE 1-continued
Illustrative Examples of the Invention
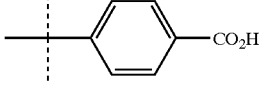
| Example No. | R | a | Ar | d | Y |
|---|---|---|---|---|---|
| 116 | 2,4,5-tri-Cl | 3 | Ph | 1 | 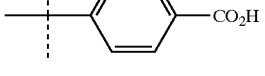 |
| 117 | 3-CONH-i-Bu | 1 | Ph | 1 | 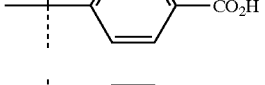 |
| 118 | 2,4-di-Me-6-Cl | 3 | Ph | 1 | 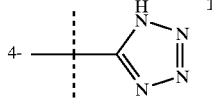 |
| 119 | 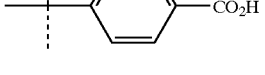 | 1 | Ph | 1 | 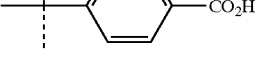 |
| 120 | 3-NO$_2$ | 1 | Ph | 1 | 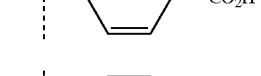 |
| 121 | 2-Cl | 1 | Ph | 1 | 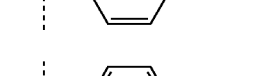 |
| 122 | 4-MeS | 1 | Ph | 1 | 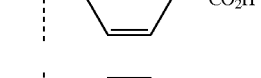 |
| 123 | 3-MeSO$_2$— | 1 | Ph | 1 | 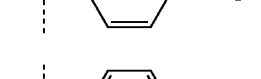 |
| 124 | 4-O—C(=O)Me | 1 | Ph | 1 | 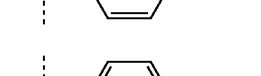 |
| 125 | 4-C(=O)Me | 1 | Ph | 1 |  |
| 126 | 3-CO$_2$H | 1 | Ph | 1 |  |
| 127 | 3-NH—SO$_2$Me | 1 | Ph | 1 |  |

TABLE 1-continued

Illustrative Examples of the Invention $$(R)_a\text{-Ar-O-CH}_2\text{-CH(OH)-CH}_2\text{-NH-(CH}_2)_d\text{-[benzofuran]-Y} \quad (I)$$

| Example No. | R | a | Ar | d | Y |
|---|---|---|---|---|---|
| 128 | 4-NH—C(=O)Me | 1 | Ph | 1 | 4-CO₂H-phenyl |
| 129 | — | 0 | pyridin-3-yl | 1 | 2-CO₂H-5-OMe-phenyl |
| 130 | — | 0 | 1H-indol-7-yl | 1 | 4-CO₂H-phenyl |
| 131 | — | 0 | 9H-carbazol-1-yl | 1 | 4-CO₂H-phenyl |
| 132 | 2-Me | 1 | quinolin-8-yl | 1 | 4-CO₂H-phenyl |
| 133 | — | 0 | benzo[b]thiophen-4-yl | 1 | 4-CO₂H-phenyl |
| 134 | — | 0 | pyridin-3-yl | 1 | 4-CO₂H-phenyl |
| 135 | — | 0 | isoquinolin-3-yl | 1 | 4-CO₂H-phenyl |

TABLE 1-continued
Illustrative Examples of the Invention
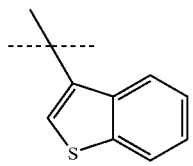
(I)
| Example No. | R | a | Ar | d | Y |
|---|---|---|---|---|---|
| 136 | — | 0 | 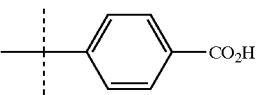 | 1 | 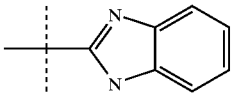 4-CO$_2$H |
| 137 | — | 0 |  | 1 | 4-CO$_2$H |
| 138 | — | 0 | Ph | 1 | 4-CO$_2$H |
| 139 | 6-NH$_2$ | 1 | 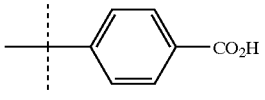 | 1 | 4-CO$_2$H |
| 140 | — | 0 | Ph | 1 | 4-CO$_2$H |
| 141 | — | 0 | Ph | 1 | 4-CO$_2$H |
| 142 | 6-NH$_2$ | 1 | 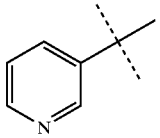 | 1 | 4-CO$_2$H |
| 143 | — | 0 | 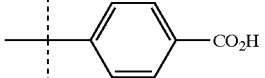 | 1 | 4-CO$_2$H |
| 144 | 6-NH$_2$ | 1 |  | 1 | 3-COOH |

TABLE 1-continued

Illustrative Examples of the Invention

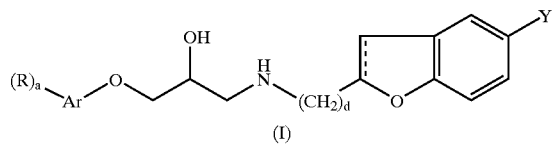

(I)

| Example No. | R | a | Ar | d | Y |
|---|---|---|---|---|---|
| 145 | — | 0 | 3-pyridyl | 1 | 6-tert-butyl-naphthalene-2-carboxylic acid |
| 146 | — | 0 | 3-pyridyl | 1 | 5-tert-butyl-2,3-dihydrobenzofuran-7-carboxylic acid |
| 147 | — | 0 | 3-pyridyl | 1 | 6-tert-butyl-naphthalene-2-carboxylic acid |
| 148 | — | 0 | 3-pyridyl | 1 | 8-tert-butyl-quinoline-2-carboxylic acid |
| 149 | — | 0 | 3-pyridyl | 1 | 2-nitro-4-tert-butyl-methylbenzene |
| 150 | — | 0 | 3-pyridyl | 1 | 1,5-dimethyl-4-tert-butyl-pyrazole-3-carboxylic acid |
| 151 | — | 0 | 3-pyridyl | 1 | 5-tert-butyl-thiophene-3-carboxylic acid methyl ester |

TABLE 1-continued

Illustrative Examples of the Invention

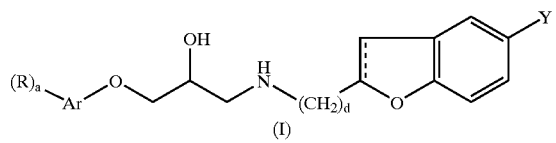
(I)

| Example No. | R | a | Ar | d | Y |
|---|---|---|---|---|---|
| 152 | — | 0 | 3-pyridyl | 1 | 4-(thiophene-2-carboxylic acid)yl |
| 153 | — | 0 | 3-pyridyl | 1 | 5-(furan-2-carboxylic acid)yl |
| 154 | — | 0 | 3-pyridyl | 2 | 2-(5-phenyl-4-ethoxycarbonyl-oxazol)yl |
| 155 | — | 0 | 3-pyridyl | 2 | 2-(4-phenyl-5-carboxy-thiazol)yl |
| 156 | — | 0 | 3-pyridyl | 1 | 6-(pyridine-3-carboxylic acid)yl |
| 157 | — | 0 | 3-pyridyl | 1 | 2-(benzothiophene-5-carboxylic acid)yl |
| 158 | — | 0 | 3-pyridyl | 2 | 3-(1-methyl-2-carboxy-indol)yl |
| 159 | — | 0 | 3-pyridyl | 1 | 2-(benzofuran-5-carboxylic acid)yl |

TABLE 1-continued

Illustrative Examples of the Invention

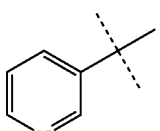

(I)

| Example No. | R | a | Ar | d | Y |
|---|---|---|---|---|---|
| 160 | — | 0 | 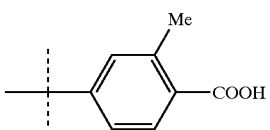 | 1 | 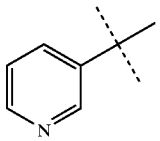 |
| 161 | — | 0 | 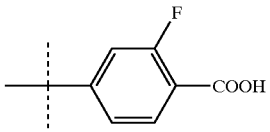 | 1 | 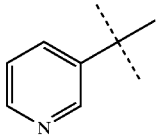 |
| 162 | — | 0 | 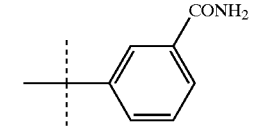 | 1 | 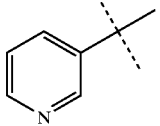 |
| 163 | — | 0 | 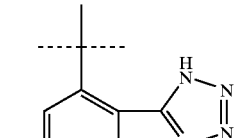 | 1 | 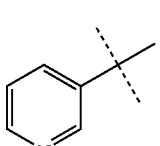 |
| 164 | — | 0 | 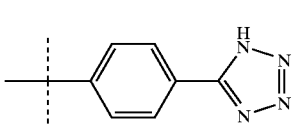 | 2 |  |

In one embodiment of the present invention, compounds of Formula I are those wherein Y is phenyl or a 5- or 6-membered heterocycle containing one or more heteroatoms each independently selected from N, S, and O, each cyclic moiety being optionally substituted with one or more substituents selected from $COR^2$, halo, and $C_1$–$C_{10}$ alkyl.

In another embodiment, compounds of Formula I are those wherein a is 0, 1, or 2; Ar is phenyl, a 5- or 6-membered heterocycle containing one heteroatom, or phenyl fused to a 5- or 6-membered heterocycle; d is 1; and Y is phenyl substituted with $COR^2$; and $R^2$ is $OR^1$.

Representative salts of the compounds of Formula I include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, undecanoate, and the like.

Base salts include, for example, alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with, for example, such agents as lower alkyl halides such as methyl, ethyl, propyl, and butyl chlorides, bromides, and iodides; dialkyl sulfates like dimethyl, diethyl, and dibutyl sulfate and diamyl sulfates; long chain halides such as decyl, lauryl, myristyl and strearyl chlorides, bromides, and iodides; aralkyl halides like benzyl and phenethyl bromides, and the like.

The esters in the present invention are non-toxic, pharmaceutically acceptable esters such as, for example, alkyl esters such as methyl, ethyl, propyl, isopropyl, butyl, isobutyl, or pentyl esters. Additional esters such as, for example, phenyl-$C_1$–$C_5$ alkyl or $C_1$–$C_5$ alkyl-O—C(—O)-$C_1$–$C_5$alkyl may be used, as well as methyl ester. The compound of Formula I may be esterified by a variety of conventional procedures including, for example, reacting the appropriate anhydride, carboxylic acid, or acid chloride with the alcohol group of the Formula I compound. The appropriate anhydride may be reacted with the alcohol in the presence of an acylation catalyst such as, for example, 1,8-bis[dimethylamino]naphthalene or N,N-dimethylaminopyridine. An appropriate carboxylic acid may be reacted with the alcohol in the presence of a dehydrating agent such as, for example, dicyclohexylcarbodiimide, 1-[3-dimethylaminopropyl]-3-ethylcarbodiimide, or other water soluble dehydrating agents which are used to drive the reaction by the removal of water, and optionally an acylation catalyst. Esterification may also be reached using the appropriate carboxylic acid in the presence of trifluoroacetic anhydride, and optionally pyridine, or in the presence of N,N-carbonyldiimidazole with pyridine. Reaction of an acid chloride with the alcohol may be carried out with an acylation catalyst such as, for example, 4-DMAP or pyridine.

Sensitive or reactive groups on the compound of Formula I may need to be protected during any of the above methods for forming esters, and protecting groups may be added and removed by conventional methods well known in the art.

One skilled in the art would readily know how to successfully carry out these as well as other methods of esterification of alcohols.

The compounds of this invention may, either by nature of asymmetric centers or by restricted rotation, be present in the form of isomers. Any asymmetric center may be in the (R)-, (S)- or (R,S) configuration, preferably in the (R)- or (S)-configuration, whichever is most active. The compounds of Formula I where the side chain containing the (R)$_a$— Ar— moiety with the hydroxy component above the plane as depicted in Formula I are preferred.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art.

Geometric isomers by nature of substituents about a double bond or a ring may be present in cis (=Z—) or trans (=E—) form, and are encompassed within the scope of this invention.

The particular process to be utilized in the preparation of the compounds of this invention depends upon the specific compound desired. Such factors as the selection of the specific Ar and Y moieties and the specific substituents on the various moieties, all play a role in the path to be followed in the preparation of the specific compounds of this invention. These factors are readily recognized by one of ordinary skill in the art.

For synthesis of any particular compound, one skilled in the art will recognize that the use of protecting groups may be required for the synthesis of compounds containing certain substituents. A description of suitable protecting groups and appropriate methods of adding and removing such groups may be found in: *Protective Groups in Organic Synthesis*, Second Edition, T. W. Greene, John Wiley and Sons, New York, 1991. For example, after preparation of a compound according to Reaction Scheme 1, in order to enable purification of the end product by, for instance, flash chromatography, compounds of Formula I wherein $R^1$ is H, may be selectively protected, for example, as a carbamate derivative obtained by, for example, treatment with a reagent such as di-tert-butyl dicarbonate or other means known in the art. After purification, the carbamate group may easily be removed by treatment with an acid such as HCl or trifluoroacetic acid by means known in the art.

In the Reaction Schemes below, one skilled in the art will recognize that reagents and solvents actually used may be selected from several reagents and solvents well known in the art to be effective equivalents. When specific reagents or solvents are shown in a Reaction Scheme, therefore, they are meant to be illustrative examples of specific, but not limiting, conditions for the execution of that particular Reaction Scheme.

General Methods of Preparation of Formula I Compounds

In general, Formula I compounds may be prepared by standard techniques known in the art and by known processes analogous thereto. In particular, three such standard methods may be used, the selection of which may be based, among other considerations, upon the commercial availability of the required individual starting materials. These three methods are illustrated in Reaction Schemes 1, 2, and 3 described below.

The compounds of Formula I where each variable may be any moiety within that variable's definition may be synthesized according to Reaction Scheme 1 by coupling an appropriate epoxide 1 with an appropriate amine 2. The epoxide of Formula 1 is either commercially available, known in the art (see, e.g., WO98/32475), or may be readily prepared from known hydroxy compounds as exemplified in Reaction Scheme 6. Preparation of 2 is described in Reaction Schemes 12 and 13 below. The reaction of Reaction Scheme 1 is typically carried out in an aprotic solvent such as dimethyl sulfoxide, dimethyl formamide, acetonitrile, or in an alcohol such as ethanol, isopropanol, or propanol at a temperature of from about –10° C. to reflux.

REACTION SCHEME 1

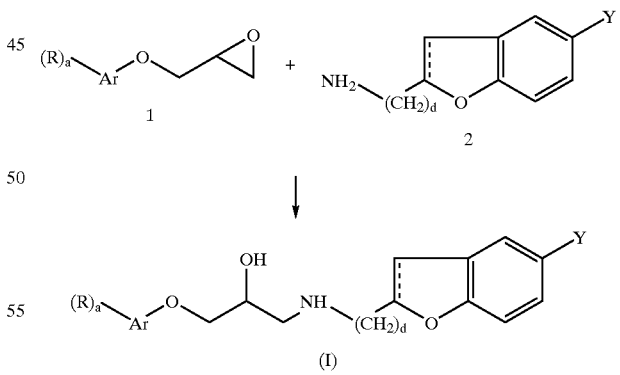

Alternatively, Formula I compounds where each variable may be any moiety within that variables definition except that d–1, may be prepared by a reductive amination as shown in Reaction Scheme 2. Reaction of an aldehyde of Formula 4 (preparation described below in Reaction Scheme 8) with an amino alcohol of Formula 3 (preparation described below in Reaction Scheme 7) followed by subsequent reduction gives the desired transformation.

REACTION SCHEME 2

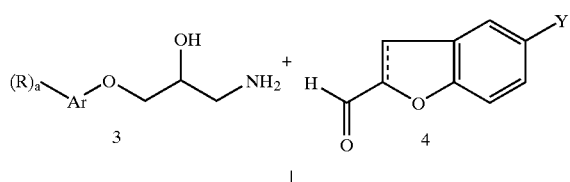

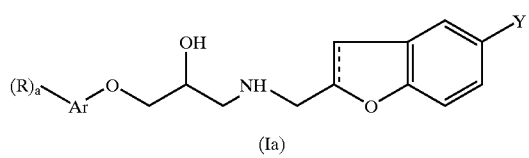

(Ia)

A third general route to Formula I compounds where each variable may be any moiety within that variable's definition except that d–1, is shown in Reaction Scheme 3. An amino alcohol 3 (Reaction Scheme 7) and a carboxylic acid 5 (preparation described in Reaction Schemes 9 and 10) are coupled to provide an amide of Formula 6. Reduction of the Formula 6 amides with an appropriate reagent such as borane-dimethylsulfide complex provides the Formula I compounds.

REACTION SCHEME 3

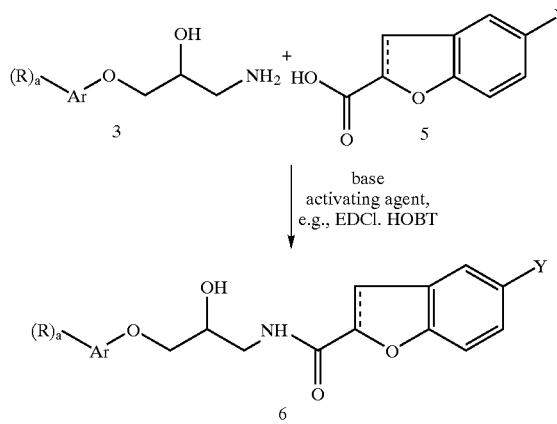

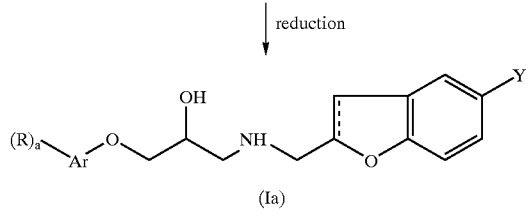

(Ia)

Compounds of Formula I where Y is a halogen, prepared by the above described methods, may in turn be used to prepare other compounds of Formula I where Y is any alkenyl, cycloalkenyl, phenyl, or a 5- or 6-membered heterocyclic ring. Methods for accomplishing this interconversion are described below in Reaction Schemes 4 and 5. For example, a compound of Formula I, wherein Y is bromo, may be prepared by Reaction Scheme 1 using corresponding starting materials 2 or 4, where Y is bromo, each of which may, in turn, be prepared by Reaction Schemes 9, 10, 12, or 14. The resulting Formula I compound is then protected by standard methods to give a compound of Formula 7a, (Y=Br) as shown in Reaction Scheme 4. The compound of Formula 7a is then converted to the boronic ester 8, which is then subjected to a Suzuki coupling reaction with a halo-Y compound of Formula 9, in which Y is any alkenyl, cycloalkenyl, phenyl, naphthyl, or a 5- or 6-membered heterocycle, to provide the corresponding Formula 7 compounds. Deprotection of Formula 7 compounds by acid or fluoride-catalyzed hydrolysis provides the corresponding Formula I compounds.

REACTION SCHEME 4

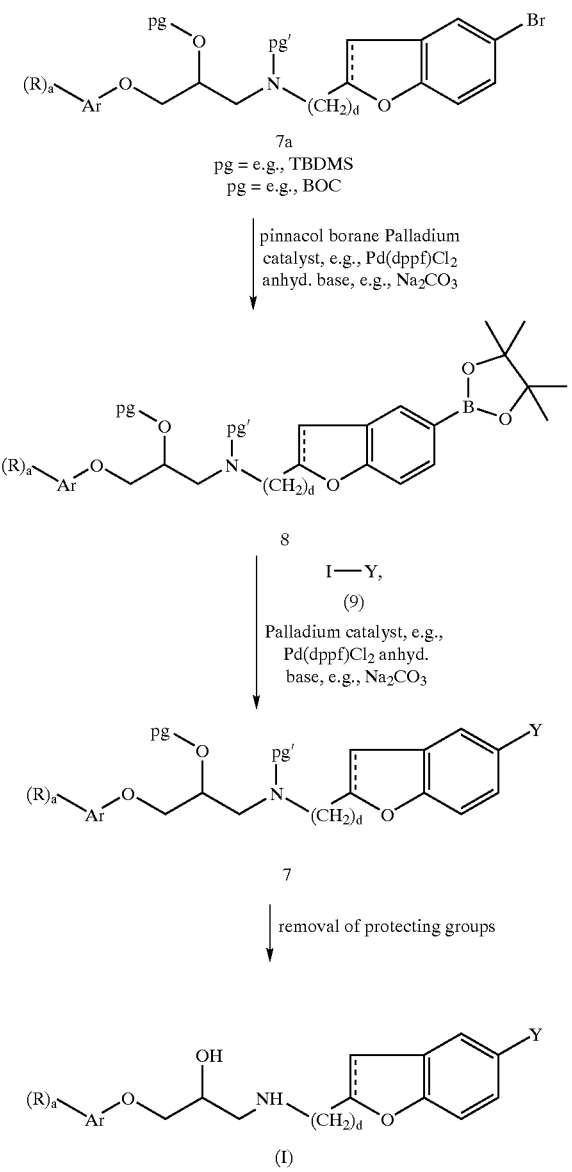

The coupling may also be performed in the reverse manner, that is, a boronic ester derivative 10, prepared from a halophenyl compound 9a, may be added to the iodo compound of Formula 7b, as shown in Reaction Scheme 5, to give Formula Ib compounds.

REACTION SCHEME 5

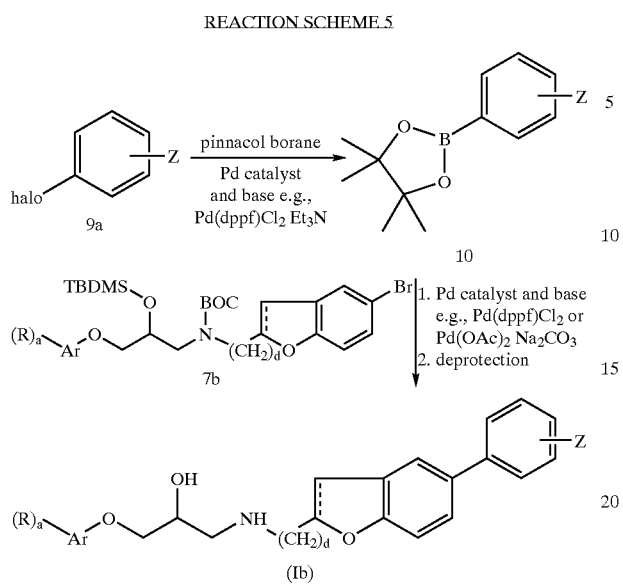

Z = $CO_2R^1$, F, $FR^1$, $OR^1$, phenyl or tetrazolo
halo = I, Cl or Br

The salts and esters of the Formula I compounds of the invention may be readily prepared by conventional chemical processes well known in the art.

General Method of Preparation of Intermediates

The starting materials required to carry out the above described reactions (e.g., epoxides 1, amines 2, amino alcohols 3, aldehydes 4, and carboxylic acids 5) are in many cases commercially available or may be readily prepared by methods known to those skilled in the art. The following routes are exemplary of such methods, but are not intended to be limiting in any way.

The epoxides 1 of Reaction Scheme 1 are commercially available or may be prepared according to one of the many procedures described in the literature known to those skilled in the art (see, e.g., WO 99/32475) from starting materials which are either commercially available or known in the art. One such general method for the preparation of Formula 1 epoxides is illustrated in Reaction Scheme 6, in which a substituted aryl or heteroaryl hydroxy compound of Formula 11, such as, for example, a phenol, hydroxypyridine, hydroxybenzofuran, hydroxyindole, hydroxyquinoline, and the like, is allowed to react with a glycidyl-, alkyl-, or arylsulfonate of Formula 12 in the presence of a strong base such as, for example, sodium hydride. The alkyl or aryl sulfonate used in this reaction may be racemic or an enantiomerically pure compound, such as (2S)-(+)- or (2R)-(−)-glycidyl tosylate, both of which are commercially available.

REACTION SCHEME 6

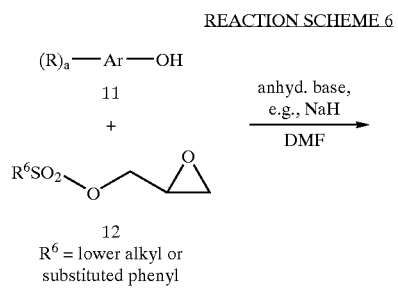

$R^6$ = lower alkyl or substituted phenyl

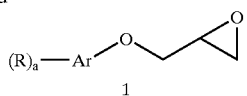

The amino alcohols 3 are either commercially available, known in the art, or may be prepared by ring opening of the epoxides 1 with a nitrogen nucleophile, such as, for example, dibenzylamine or phthalimide, in presence of a base. Removal of the phthalimide by cleavage with hydrazine or the benzyl groups by hydrogenolysis provides the desired amino alcohol of Formula 3. An example of this is shown in Reaction Scheme 7.

REACTION SCHEME 7

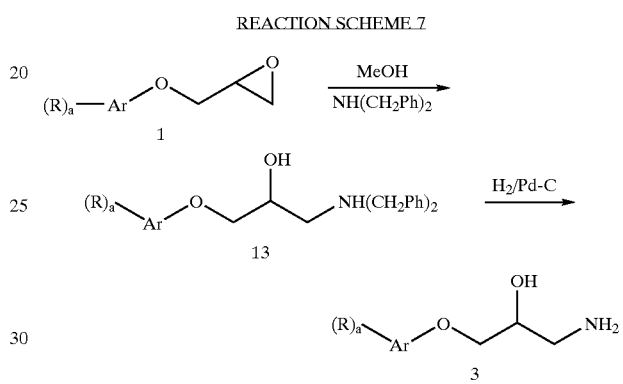

Synthesis of aldehyde starting materials of Formula 4 may be accomplished by oxidation of alcohols of formula 14, for example, under Swern conditions as shown in Reaction Scheme 8.

REACTION SCHEME 8

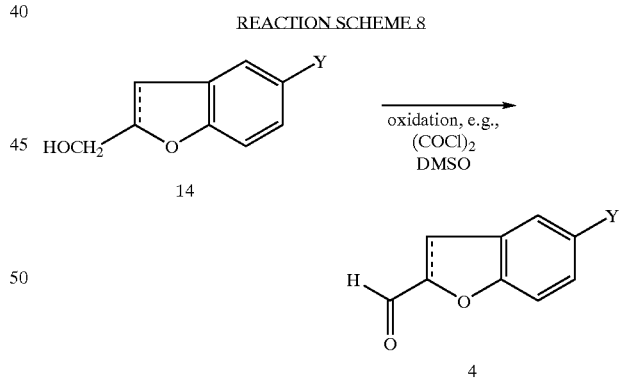

Compounds of Formula I where --- represents double bond may be prepared from corresponding intermediates in which --- represents a double bond. Examples of intermediates where --- represents a double bond are, for example, benzofuran acids of Formula 5a, benzofuran esters of 17a, and benzofuran alcohols of formula 14a. Utilizing a known benzofuran synthesis (Yoo et al., Bioorg. Med. Chem. 5:445, 1997), benzofuran esters 17a may be prepared from commercially available benzaldehydes, and hydrolyzed to 5a or reduced to 14a as shown in Reaction Scheme 9.

REACTION SCHEME 9

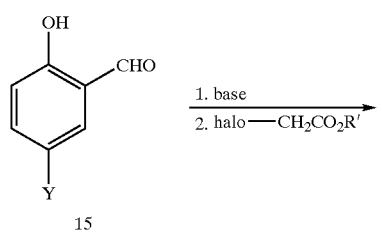

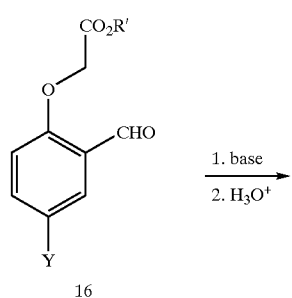

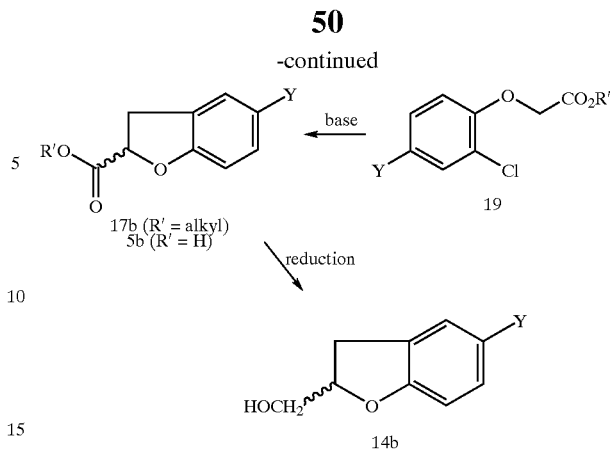

Likewise, compounds of Formula I where --- represents a single bond may be prepared from intermediates where --- represents a single bond. For example, dihydrobenzofuran esters of formula 17b, may be prepared from the intermediate 16 by reduction, halogen substitution, and cyclization as shown in Reaction Scheme 10. The corresponding dihydrobenzofuran acids of Formula 5b may be obtained hydrolysis of the Formula 17b esters. Reduction of 17b gives the dihydrobenzofuran alcohol of Formula 14b.

REACTION SCHEME 10

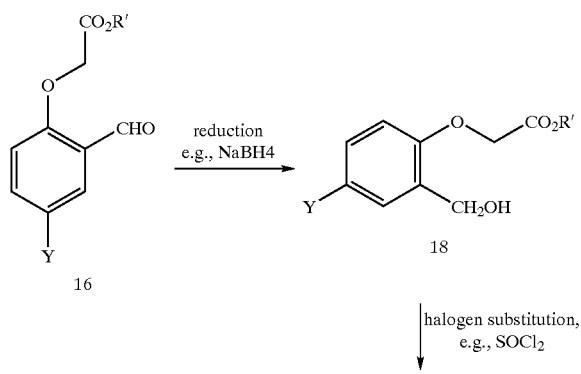

In the case of either Reaction Scheme 9 or 10, if Y is a halogen atom, the alcohol products 14a or 14b may be protected as compounds of Formula 20 and used to prepare a variety of other Formula 14 alcohols where Y is other than halogen. This is exemplified in Reaction Scheme 11 for the preparation of compounds of Formula 14, where Y is any alkenyl, cycloalkenyl, phenyl, naphthyl, or a 5- or 6-membered heterocycle. Conversion of 20a to the corresponding benzofuran or dihydrobenzofuran boronic ester of Formula 21, followed by Suzuki coupling of 21 with a halo-Y compound of Formula 9 yields, after hydrolysis, the Formula 14 alcohols.

REACTION SCHEME 11

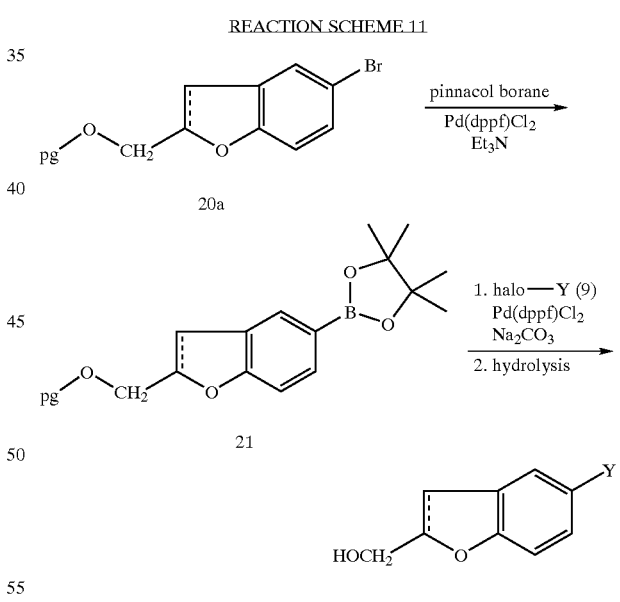

pg = e.g., TBDMS
halo = I, Cl or Br
R' = lower alkyl

The amine starting materials of Formula 2 in which d–1 are generally available by standard methods involving conversion of a carboxylic acid 5 to an amide of Formula 22 and reduction with borane. This sequence is shown in Reaction Scheme 12 for Formula 2 amines wherein d–1.

REACTION SCHEME 12

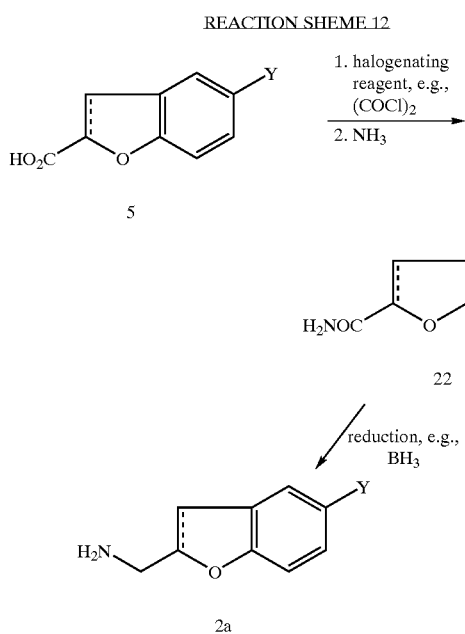

Formula 2 amines in which d is 2 may be prepared by standard homologation sequences of known intermediates where d=1. For example, aldehydes of Formula 4 can undergo an alkyl chain extension according to well known procedures such as that described by Wittig et al., (Chem. Ber., 2514, 1962), and the process may be repeated in order to prepare the acetic and propionic acid homologues of Formula 5. These chain-extended acids may be used in place of the acid of Formula 5 by a method analogous to Reaction Scheme 12, to provide a variety of Formula 2 amines in which d=2.

Formula 2 amines in which Y is other than hydrogen or halo may be prepared by palladium-catalyzed coupling reactions on the N-protected amine of Formula 23a, followed by deprotection, as shown in Reaction Scheme 13. Formula 2 amines prepared in this way in which the Y group is substituted by an acid, ester, alcohol, ketone, sulfide, or nitro group can also provide additional Formula 2 amines by manipulation of that functional group by directed hydrolysis, esterification, reduction, oxidation, and/or reduction reactions, and the like.

REACTION SCHEME 13

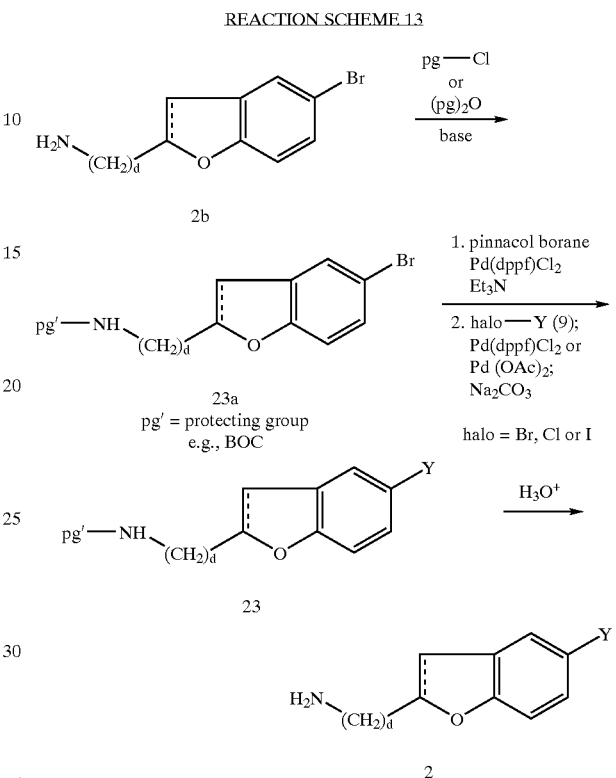

Dihydrobenzofuran alcohols of Formula 14b, where --- represents a single bond and Y is a halogen, carboxylic acid, or ester may be prepared from Formula 20b compounds where Y is hydrogen, via halogenation, for example, iodination, carbonylation, and deprotection steps, as exemplified in Reaction Scheme 14.

REACTION SCHEME 14

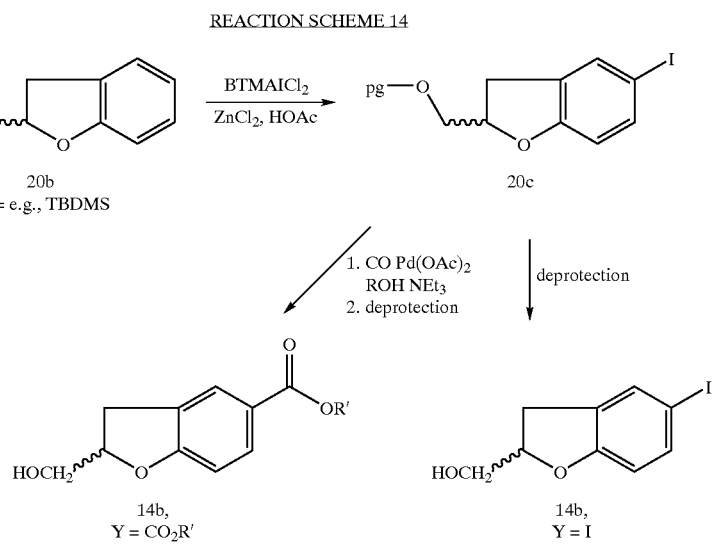

Compounds of Formula 14 where Y is an alkenoic or alkanoic acid or ester may be prepared from Formula 20 compounds (protected forms of Formula 14a or 14b), where Y is halogen. An example of this sequence involves palladium-catalyzed coupling of 20a with an Palkenoic acid derivative, as shown in Reaction Scheme 15. Reduction of the double bond in the product 20d provides compound of Formula 20e. Deprotection of 20d and 20e provides the corresponding Formula 14 alcohols which are converted to Formula I compounds as described above.

REACTION SCHEME 15

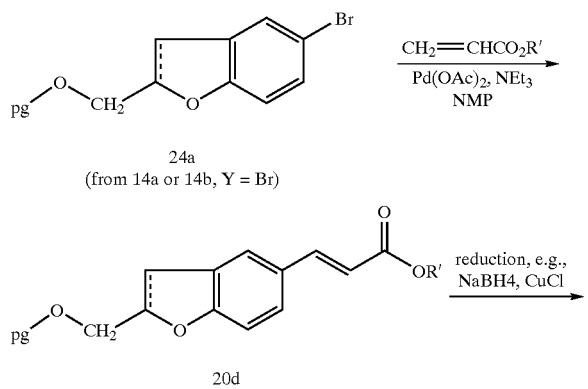

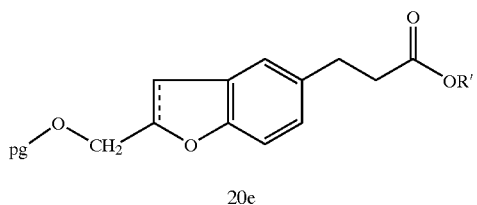

20e

R' is alkyl or H

Alcohol intermediates of Formula 14 in which Y is other than hydrogen or halo may also be prepared from the bromo alcohols, 14a or 14b (Y=Br), as shown in Reaction Scheme 16, by a procedure analogous to the previously described Suzuki coupling methodology of Reaction Schemes 4, 11, and 13. This may be accomplished either directly, or via a 4-step sequence involving protection of the Formula 14a or 14b (Y=Br) alcohol, for example, as a t-butyldimethylsilyl ether 20f, conversion of this compound to a boronic ester, and Suzuki coupling reaction of the boronic ester with a halo-Y compound of Formula 2 compound to 20g, and finally deprotection to 14.

REACTION SCHEME 16

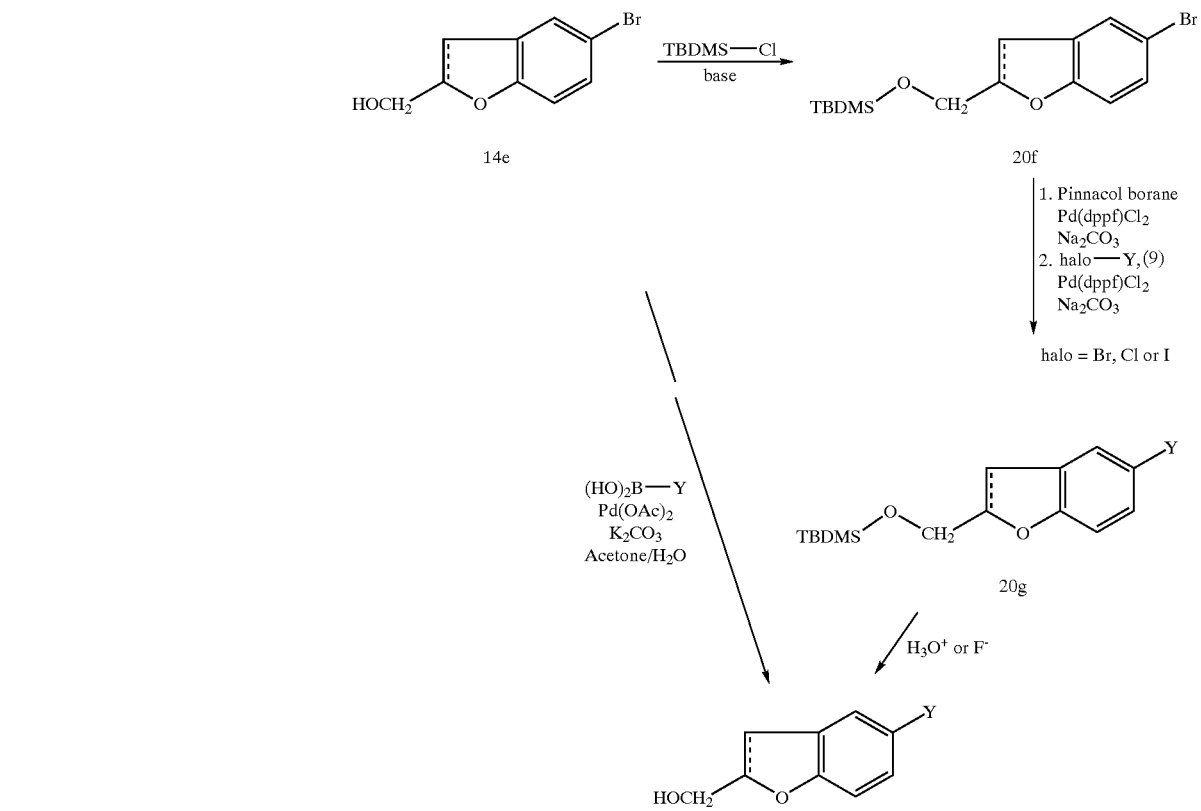

The halo-Y compounds of Formula 9 where halo is iodo, chloro, or bromo and Y is any alkenyl, cycloalkenyl, phenyl, naphthyl, or a 5- or 6-membered heterocycle, used in Reaction Schemes 4, 11, 13, and 16, are either commercially available or synthesized by standard methods known to those skilled in the art. One such standard method is direct halogenation of a known H—Y compound with a halogenating agent; other methods include the functional group conversion of HO—Y, NH$_2$—Y compounds to halo-Y compounds by standard substitution methods. A particular illustration is the preparation of halo-Y compounds of Formula 9b and 9c where Y represents an oxazole or a thiazole, prepared by direct halogenation of the unsubstituted compound 24, or by diazotization of a NH$_2$—Y compound 26 as shown in Reaction Scheme 17.

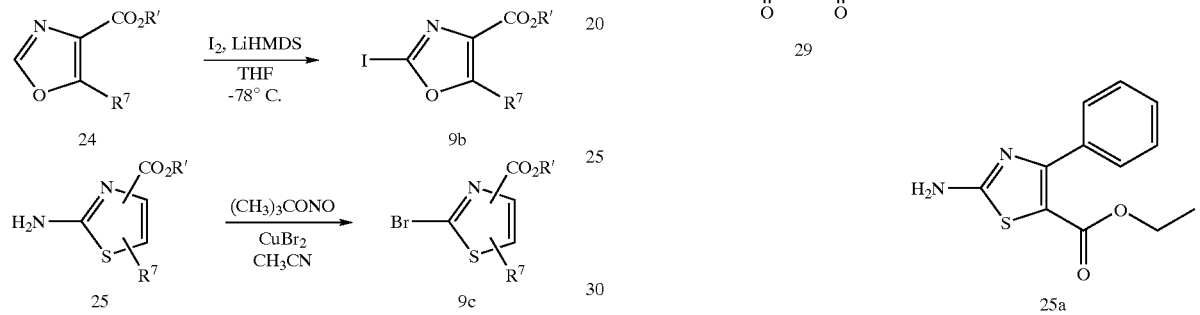

R' = lower alkyl
R' = lower alkyl or substituted phenyl

The heterocyclic intermediates, 24 and 25, used to prepare 9b and 9c are accessible by standard methods from acyclic materials, for example, by the reactions as shown in Reaction Schemes 18, 19, and 20.

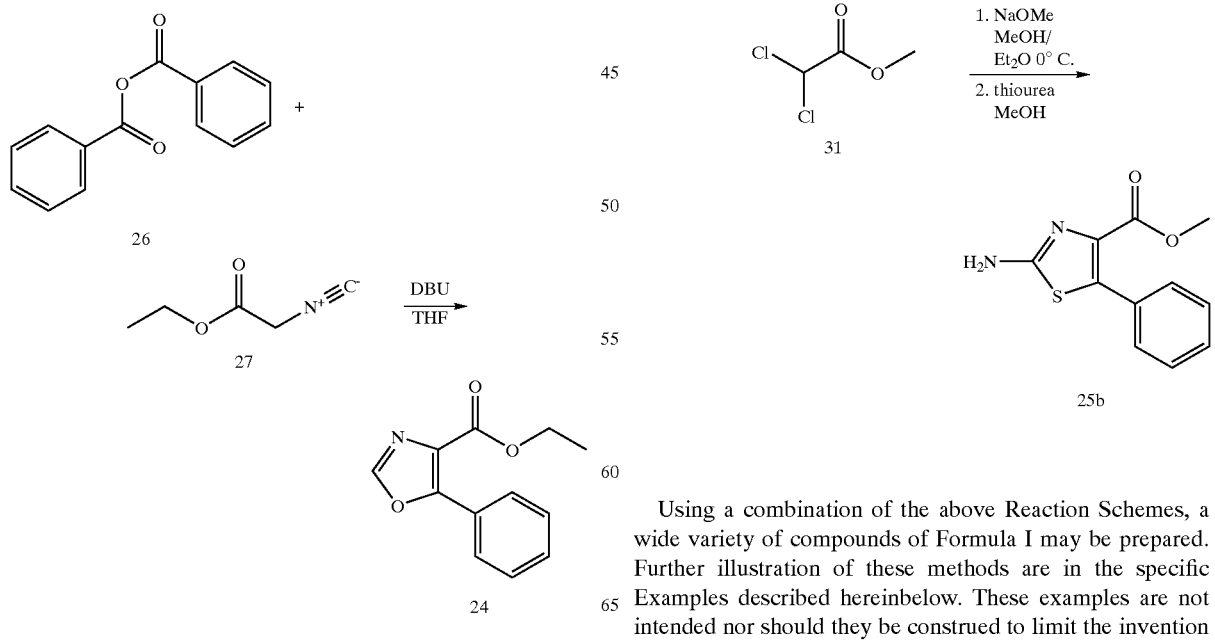

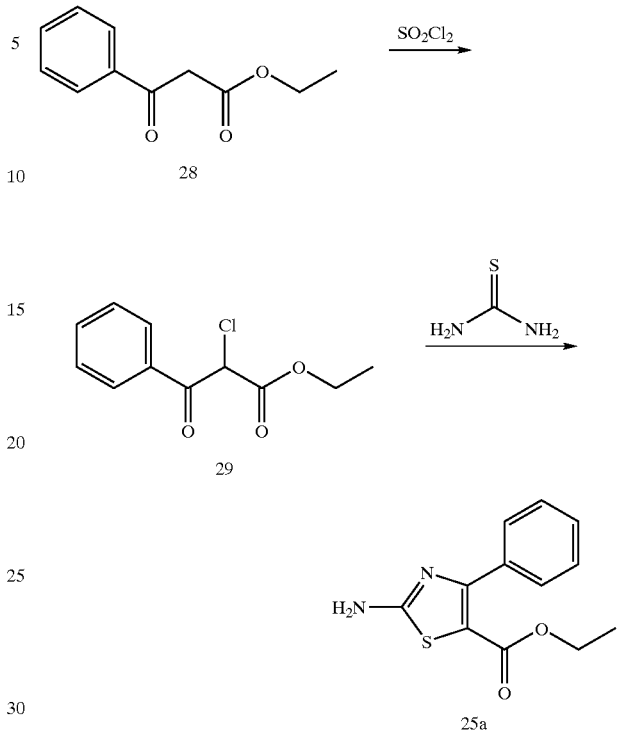

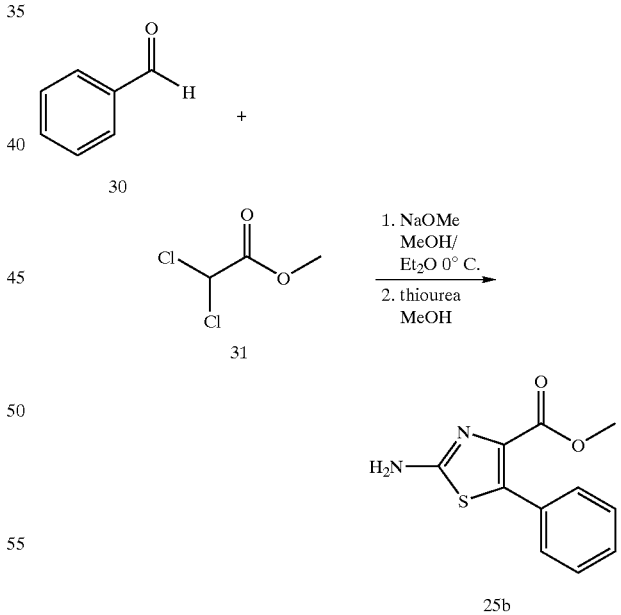

Using a combination of the above Reaction Schemes, a wide variety of compounds of Formula I may be prepared. Further illustration of these methods are in the specific Examples described hereinbelow. These examples are not intended nor should they be construed to limit the invention in any way.

ABBREVIATIONS AND ACRONYMS

When the following abbreviations are used herein, they have the following meaning:

| | |
|---|---|
| Ac$_2$O | acetic anhydride |
| anhyd. | anhydrous |
| BH$_3$ | borane |
| BOC | tert-butyloxycarbonyl |
| BTMAICl$_2$ | benzyltrimethylammonium dichloriodate |
| n-BuLi | n-butyllithium |
| t-BuLi | t-butyllithium |
| Cbz | benzyloxycarbonyl |
| CDI | carbonyldiimidazole |
| Celite ® | diatomaceous earth filter agent, ® Celite Corp. |
| CI-MS | chemical ionization mass spectroscopy |
| conc. | concentrated |
| mCPBA | 3-chloroperoxybenzoic acid |
| dec. | decomposition |
| DBU | 1,8-diazabicyclo[5.4.0]undec-7-ene |
| DMAP | 4-dimethylaminopyridine |
| DME | dimethoxyethane |
| DMF | N,N-dimethylformamide |
| DMSO | dimethylsulfoxide |
| EDCI | 1-(3-dimethylaminopropyl)-3-ethylcarbodiimide |
| EtOAc | ethyl acetate |
| EtOH | ethanol (100%) |
| Et$_2$O | diethyl ether |
| Et$_3$N | triethylamine |
| HOBT | 1-hydroxybenzotriazole hydrate |
| HPLC ES-MS | high performance liquid chromatography-electrospray mass spectroscopy |
| KOtBu | potassium tert-butoxide |
| LiAlH$_4$ | lithium aluminum hydride |
| LiBH$_4$ | lithium borohydride |
| LiHMDS | lithium bis(trimethylsilyl)amide |
| MeCN | acetonitrile |
| MeOH | methanol |
| MSTFA | N-methyl-N-(trimethylsilyl)trifluoroacetamide |
| Na(OAc)$_3$BH | sodium triacetoxyborohydride |
| NaBH$_4$ | sodium borohydride |
| NMM | 4-methylmorpholine |
| Ph$_3$P | triphenylphosphine |
| Pd(dppf)Cl$_2$ | [1,1'-bis(diphenylphosphino)ferrocene]dichloropalladium(II) |
| Pd(PPh$_3$)$_4$ | tetrakis(triphenylphosphine)palladium(0) |
| Pd(OAc)$_2$ | palladium acetate |
| rt | room temperature |
| pg | protecting group |
| TBAF | tetrabutylammonium fluoride |
| TBDMS | tert-butyldimethylsilyl |
| TBDMSCl | tert-butyldimethylsilyl chloride |
| TBDMSOTf | tert-butyldimethylsilyl trifluoromethanesulfonate |
| THF | tetrahydrofuran |
| TFA | trifluoroacetic acid |
| TLC | thin layer chromatography |

General Experimental Procedures

HPLC-electrospray mass spectra (HPLC ES-MS) were obtained using a Hewlett-Packard 1100 HPLC equipped with a quaternary pump, a variable wavelength detector, a YMC Pro C18 2.0 mm×23 mm column, and a Finnigan LCQ ion trap mass spectrometer with electrospray ionization. Gradient elution from 90% A to 95% B over 4 minutes was used on the HPLC. Buffer A was 98% water, 2% Acetonitrile, and 0.02% TFA. Buffer B was 98% Acetonitrile, 2% water, and 0.018% TFA. Spectra were scanned from 140–1200 amu using a variable ion time according to the number of ions in the source.

$^1$H NMR spectra were determined at 300 MHz using a General Electric GE-OMEGA 300 spectrometer. Chemical shifts are reported in parts per million (δ) values relative to tetramethylsilane as internal standard. Spin multiplicities are reported using the following abbreviations: singlet (s), doublet (d), triplet (t), quartet (q), multiplet (m), and broad (br) Coupling constants are in Hertz.

Melting points were recorded in open capillary tubes and are uncorrected.

EXAMPLE 1

Preparation of Ethyl(4-bromo-2-formylphenoxy) acetate

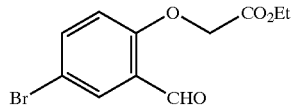

This compound was prepared according to a literature procedure (Yoo et al., Bioorg. Med. Chem. 5:445, 1997). 5-Bromo-2-hydroxybenzaldehyde (10.0 g, 49.7 mmol) was dissolved in 90 mL anhyd. DMF and the mixture was cooled to 0° C. NaH (60% dispersion in mineral oil, 2.38 g, 59.6 mmol) was added in portions and the reaction was stirred at 0° C. for 1 hour. Ethyl bromoacetate (9.95 g, 59.6 mmol) was then added dropwise over 10 minutes and the reaction was stirred at rt overnight (18 hours). After this time, 30 mL of 1 N HCl was added to adjust the pH to acidity, and the reaction mixture was transferred to a separatory funnel and extracted with EtOAc (3×60 mL). The combined organics rinsed with water (2×40 mL), dried over MgSO$_4$, filtered, and concentrated in vacuo to provide a thick oil. Purification by flash chromatography (10% EtOAc/hexanes) provided the product as a clear oil (14.0 g, 98%). $^1$H-NMR (CD$_2$Cl$_2$, δ): 1.29 (t, 3H), 4.26 (q, 2H), 4.78 (s, 2H), 6.83 (d, 1H), 7.65 (dd, 1H), 7.94 (s, 1H), 10.47 (s, 1H); LRMS (GC/MS/EI) 286 [M]$^+$.

EXAMPLE 2

Preparation of Ethyl 5-Bromo-1-benzofuran-2-carboxylate

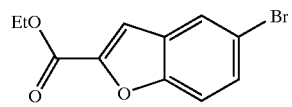

The compound was prepared according to a literature procedure. (Yoo et al., Bioorg. Med. Chem. 5:445, 1997). To ethyl (4-bromo-2-formylphenoxy)acetate (Example 1, 14.3 g, 49.7 mmol) was added, under Ar, 115 mL absolute EtOH. To this mixture was added 5.28 g (77.7 mmol) sodium ethoxide and the reaction allowed to reflux overnight. Sulfuric acid (conc., 2 mL) was then added, and the reaction allowed to reflux an additional 2 hours. The mixture was then cooled to rt, 50 mL was added and the pH adjusted to neutrality with 1 N NaOH. The mixture was then extracted with 150 mL EtOAc, and the combined organic phase was washed with brine (2×150 mL), dried over Na$_2$SO$_4$, and filtered. The solvent was removed in vacuo. Purification by Biotage® separation using 5% EtOAc/hexanes provided 3.62 g (27%) of the desired compound. $^1$H-NMR (CDCl$_3$, 67): 1.43 (t, 3H), 4.45 (q, 2H), 7.46–7.57 (m, 3H), 7.82 (s, 1H); LRMS (GC/MS/EI) 268 [M]$^+$.

EXAMPLE 3

Preparation of (S-bromo-1-benzofuran-2-yl) methanol

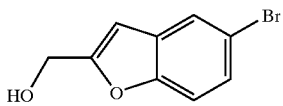

Ethyl 5-bromo-1-benzofuran-2-carboxylate (Example 2, 1.0 g, 3.7 mmol) in 90 mL absolute EtOH under Ar was cooled to 0° C. and 424 mg (11.2 mmol) sodium borohydride was added. The reaction heated to reflux for 1 hour, after which time TLC (5% EtOAc/hexanes) indicated no remaining starting material. The EtOH was removed in vacuo and 1 N HCl was added dropwise until a pH=2 was reached. The mixture was transferred to a separatory funnel and 50 mL water was added. The mixture was extracted with EtOAc (3×60 mL), the organic extracts were dried over $Na_2SO_4$, filtered, and concentrated in vacuo to provide the pure product in quantitative yield. $^1$H-NMR (CDCl$_3$, δ): 4.77 (s, 2H), 6.62 (s, 1H), 7.25–7.58 (m, 3H), 7.67 (s, 1H; LRMS (GC/MS/EI) 226 [M]$^+$.

EXAMPLE 4

Preparation of Methyl 4-[2-(hydroxymethyl)-1-benzofuran-5-yl]benzoate

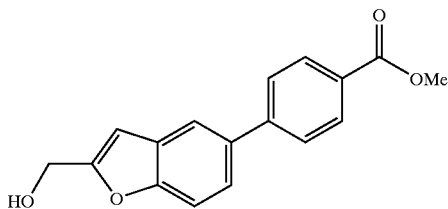

To 4 mL DME under Ar was added (5-bromo-1-benzofuran-2-yl)methanol (Example 3, 250 mg, 1.10 mmol) and Ar was bubbled through the mixture for 2 minutes to remove any dissolved oxygen. To this mixture was then added 37.6 mg (0.033 mmol) tetrakis(triphenylphosphine) palladium(0) and the reaction was stirred for 10 minutes at rt. 4-(Methoxycarbonyl)phenyl boronic acid (218 mg, 1.21 mmol) and 2.64 mL of 1 M $Na_2CO_3$ were then added, and the mixture was then heated to 100° C. for 2.5 hours under Ar. At the end of this time, TLC (5% MeOH/CH$_2$Cl$_2$) revealed complete reaction. The mixture was then filtered and the DME removed under reduced pressure. The thick paste was then transferred to a separatory funnel with 80 mL water and 100 mL EtOAc. The EtOAc was separated and the aqueous phase extracted with EtOAc (2×100 mL). The combined organic layers were dried over $Na_2SO_4$, filtered, and solvent removed in vacuo to provide a dark brown solid. The solid was dissolved in a minimal amount of MeOH, fused to silica gel, and purified by flash chromatography (2.5% MeOH/CH$_2$Cl$_2$). The desired product (247.7 mg, 80%) was obtained as a white solid. $^1$H-NMR (acetone-d$_6$, δ: 3.91 (s, 3H), 4.71 (s, 2H), 6.82 (s, 1H), 7.62 (m, 2H), 7.83 (d, 2H), 7.94 (m, 1H), 8.09 (d, 2H); LRMS (GC/MS/EI) 282 [M]$^+$.

EXAMPLE 5

Preparation of Methyl 4-(2-formyl)-1-benzofuran-5-yl)benzoate

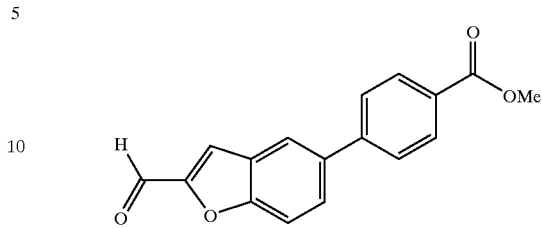

Oxalyl chloride (146 mg, 1.15 mmol) in 10 mL CH$_2$Cl$_2$ under Ar was cooled to −78° C. and 140 mg (1.79 mmol) DMSO was added dropwise. The mixture was stirred for 30 minutes at −78° C., and a solution of methyl 4-[2-hydroxymethyl)-1-benzofuran-5-yl]benzoate (Example 4, 202 mg, 0.716 mmol) in 10 mL CH$_2$Cl$_2$ was added dropwise. After 4 hours, triethylamine (435 mg, 4.30 mmol) was added and the reaction allowed to warm to rt overnight. The volatiles were removed under reduced pressure resulting in a thick paste which was purified by flash chromatography (0–2% MeOH/CH$_2$Cl$_2$) to provide the product as a thick oil (167.3 mg, 82%). $^1$H-NMR (CD$_2$Cl$_2$, δ): 3.94 (s, 3H), 7.67 (s, 1H), 7.74 (m, 3H), 7.84 (m, 1H), 8.03 (s, 1H), 8.13 (d, 2H), 9.89 (s, 1H); LRMS (GC/MS/EI) 280 [M]$^+$.

EXAMPLE 6

Preparation of 4-[2-({[(2S)-2-hydroxy-3-phenoxypropyl]amino}methyl)-1-benzofuran-5-yl]benzoic acid, hydrochloride

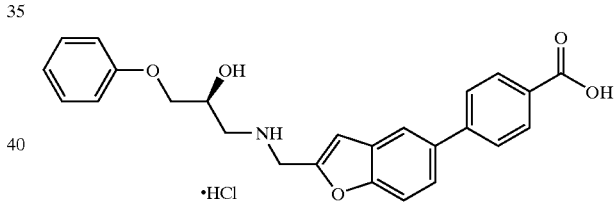

To methyl 4-(2-formyl-1-benzofuran-5-yl)benzoate (Example 5, 106 mg, 0.380 mmol) in 10 mL CH$_2$Cl$_2$, was added (2S)-1-amino-3-phenoxy-2-propanol (76.2 mg, 0.455 mmol) and the mixture cooled to 0° C. Glacial acetic acid (0.2 mL) was added, the mixture was stirred at rt for 2 hours, then Na(OAc)$_3$BH (241 mg, 1.14 mmol) was added, and the reaction was stirred at rt overnight (17 hours). The reaction mixture was adjusted to pH 10.5 with 2 M K$_2$CO$_3$, the mixture was transferred to a separatory funnel and diluted with 10 mL water. The CH$_2$Cl$_2$ was separated and the aqueous phase extracted with CH$_2$Cl$_2$ (3×20 mL) and EtOAc (2×20 mL). The combined organic layers were dried over Na$_2$SO$_4$, filtered, and concentrated in vacuo. Purification by HPLC (5–90% MeCN/water+0.1% TFA) provided 76 mg (37%) of the methyl ester of the product as a TFA salt. $^1$H-NMR (CD$_3$OD, δ): 3.40 (dd, 1H), 3.26 (dd, 1H), 3.93 (s, 3H), 4.05 (dd, 1H), 3.98 (dd, 1H), 4.29 (m, 1H), 4.56 (s, 2H), 6.93 (m, 3H), 7.15 (s, 1H), 7.26 (dd, 2H), 7.71 (dd, 1H), 7.64 (d, 1H), 7.97 (s, 1H), 8.10 (d, 1H); LRMS (LC/MS/+esi) 232.1 [M+H]$^+$.

The ester TFA salt was then suspended in 10 mL MeOH, 2 mL water, and 1.04 mL of 1 M NaOH. The mixture was heated to 100° C. and the solid dissolved. The mixture was stirred overnight, the MeOH was removed in vacuo, and the pH adjusted to 1–2 with 1 M HCl. The desired product was precipitated and was removed by filtration, providing 47.3 mg (80%) as a HCl salt. $^1$H-NMR (CD$_3$OD, δ): 3.40 (dd, 1H), 3.25 (dd, 1H), 4.05 (dd, 1H), 3.99 (dd, 1H), 6.94 (m, 3H), 7.15 (s, 1H), 7.26 (dd, 2H), 7.65 (d, 1H), 7.72 (dd, 1H), 7.77 (d, 2H), 7.97 (s, 1H), 8.10 (d, 2H); LRMS (LC/MS/+esi) 418.1 [M+H]$^+$.

EXAMPLE 7

Preparation of ethyl [4-bromo-2-(hydroxymethyl) phenoxy]acetate

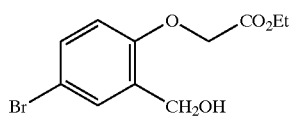

Ethyl (4-bromo-2-formylphenoxy)acetate (Example 1, 6.00 g, 21.0 mmol) in 200 mL abs EtOH was stirred under Ar and the mixture was cooled to 0° C. To this mixture was added NaBH$_4$ (199 mg, 5.24 mmol) in portions. The reaction was stirred for 1 hour where TLC (25% EtOAc/hexanes) revealed complete reaction. At this point, 1 N HCl was added dropwise until slightly acidic and the EtOH was removed under reduced pressure. Water (100 mL) was added and the reaction transferred to a separatory funnel where it was extracted 3×100 mL with EtOAc. The combined organic layers were dried over Na$_2$SO$_4$, filtered, and removed in vacuo to provide the product (5.41 g, 89%) as a pure white solid. $^1$H-NMR (acetone-d$_6$, δ): 1.24 (t, 3H), 4.21 (q, 2H), 4.76 (s, 2H), 4.85 (s, 2H), 6.98 (d, 1H), 7.46 (dd, 1H); 7.61 (d, 1H); LRMS (GC/MS/EI) 308 [M]$^+$.

EXAMPLE 8

Preparation of Ethyl [4-bromo-2-(chloromethyl) phenoxy]acetate

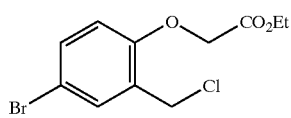

To ethyl [4-bromo-2-(hydroxymethyl)phenoxy]acetate (Example 7, 5.00 g, 17.4 mmol) in 150 mL CH$_2$Cl$_2$ under Ar, was added SOCl$_2$ (4.13 g, 34.7 mmol) dropwise with stirring. The mixture was then heated to reflux for 4 hours, cooled, and the volatiles were removed under reduced pressure. The crude oil was then subjected to flash chromatography (15% EtOAc/hexanes) to provide 4.02 g (76%) of the desired product as a clear oil. $^1$H-NMR (acetone-d$_6$, δ): 1.25 (t, 3H), 3.50 (ddd, 2H), 4.22 (q, 2H), 5.37 (dd, 1H), 6.77 (d, 1H), 7.29 (m, 1H), 7.37 (m, 1H); LRMS (GC/MS/EI) 270 [M]$^+$.

EXAMPLE 9

Preparation of Ethyl 5-bromo-2,3-dihydro-1-benzofuran-2-carboxylate

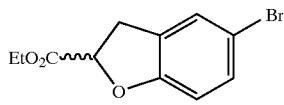

In a manner similar to the procedure described for the preparation of Example 2 and using the compound of Example 8 as starting material, the product was obtained (206 mg, 47%) and was isolated as a white solid. $^1$H-NMR (acetone-d$_6$, δ): 1.25 (t, 3H), 3.37 (dd, 1H), 3.63 (dd, 1H), 4.20 (q, 2H), 5.30 (dd, 2H), 6.77 (m, 2H), 7.28 (m, 1H); LRMS (LC/MS/+esi) 272.8 [M]$^+$.

EXAMPLE 10

Preparation of (5-bromo-2,3-dihydro-1-benzofuran-2-yl)methanol

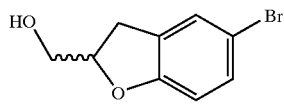

The compound was prepared following the procedure for the preparation of Example 3, using the compound of Example 9 as starting material. The product (173 mg, 99%) was isolated as a white solid. $^1$H-NMR (CD$_3$OD, δ): 3.11 (ddd, 2H), 3.69 (ddd, 2H), 4.84 (m, 1H), 6.83 (d, 1H), 7.17 (m, 1H), 7.27 (m, 1H); LRMS (GC/MS/EI) 228 [M]$^+$.

EXAMPLE 11

Preparation of Methyl 4-[2-(hydroxymethyl)-2,3-dihydro-1-benzofuran-5-yl]benzoate

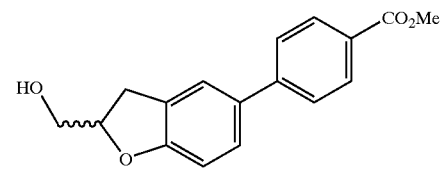

The compound was prepared following the procedure for the preparation of Example 4, using the compound of Example 10 as starting material. The product (118 mg, 55%) was isolated as a white solid. $^1$H-NMR (CDCl$_3$, δ): 3.20 (ddd, 2H), 3.83 (ddd, 2H), 3.93 (s, 3H), 4.99 (m, 1H), 6.87 (d, 2H), 7.58 (m, 3H), 8.06 (d, 2H); TLC (10% MeOH/90% CH$_2$Cl$_2$, UV) R$_f$=0.48.

EXAMPLE 12

Preparation of 4-[2-(2-{[(2S)-2-hydroxy-3-phenoxypropyl]}ethyl)-2,3-dihydro-1-benzofuran-5-yl]benzoic acid, hydrochloride

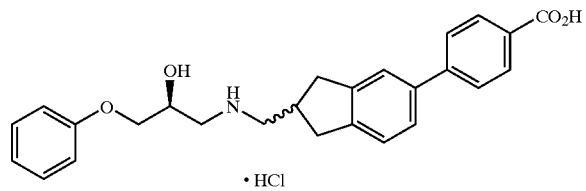

· HCl

To CH$_2$Cl$_2$ (5 mL) was added oxalyl chloride (84 mg, 0.66 mmol). The mixture was cooled to −78° C., DMSO (82.0 mg, 1.05 mmol) was added dropwise and the reaction was stirred for 10 minutes. Methyl 4-[2-(hydroxymethyl)-2,3-dihydro-1-benzofuran-5-yl]benzoate (Example 11, 118 mg, 0.415 mmol) was added as a solution in 4 mL CH$_2$Cl$_2$, the reaction was stirred for 3 hours, and triethylamine (255 mg, 2.52 mmol) was then added. After 30 minutes at −78° C., the reaction mixture was allowed to warm to rt. (2S)-1-Amino-3-phenoxy-2-propanol (82.3 mg, 0.492 mmol) was added, followed by glacial acetic acid (197 mg, 3.28 mmol, 0.19 mL). This mixture was stirred for 1.5 hours, Na(OAc)$_3$BH (261 mg, 1.23 mmol) was added, and the reaction was stirred at rt overnight. The pH was adjusted to 10.5 with 2 M K$_2$CO$_3$, and the mixture transferred to a separatory funnel and extracted 3×20 mL with CH$_2$Cl$_2$ and 2×20 mL with EtOAc. The combined organic layers were dried over anhyd. Na$_2$SO$_4$ and filtered, and the solvent was removed in vacuo. The solid was then dissolved in MeOH, fused to silica gel, and purified by flash chromatography (5% 2 M NH$_3$ in MeOH/95% CH$_2$Cl$_2$) to provide 95.8 mg (54%) of the methyl ester of the desired product. $^1$H-NMR (DMSO-d$_6$, δ): 2.35–3.41 (m, 5H), 3.85 (m, 5H), 4.93(m, 1H), 5.03 (br s, 1H), 6.86 (m, 4H), 7.23 (m, 2H), 7.53 (m, 3H), 7.72 (d, 2H), 7.95 (d, 2H); LRMS (LC/MS/+esi) 434.3 [M]$^+$.

Treatment of the methyl ester was performed according to the procedure described for the saponification of the methyl ester of Example 6, yielding 57.7 mg (60%) of final product. $^1$H-NMR (DMSO-d$_6$, δ): 3.06 (m, 2H), 3.34 (m, 4H), 3.96 (m, 2H), 4.32 (m, 1H), 5.25 (m, 1H), 6.21 (br s, 1H), 6.90 (m, 4H), 7.29 (m, 2H), 7.53 (m, 3H), 7.71 (d, 2H), 7.96 (d, 2H), 12.87 (br s, 1H); LRMS (LC/MS/+esi) 420.4 [M]$^+$.

EXAMPLE 13

Preparation of Ethyl 4-(4,4,5,5-tetramethyl-1,3,2-dioxaborolan-2-yl)benzoate

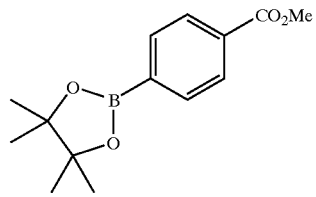

A solution of methyl 4-iodobenzoate (2.00 g, 7.63 mmol) in 30 mL dioxane was degassed with Ar for 10 minutes. Then, Pd(dppf)Cl$_2$ (171 mg, 3 mol %) triethylamine (3.27 mL), and pinacolborane (1.47 g, 11.45 mmol) were added. The resulting solution was stirred at 85° C. for 16 hours. The mixture was allowed to cool to ambient temperature, filtered through a pad of Celite®, and concentrated in vacuo to obtain 3.97 g of product which was used without further purification. m/z=263 [M+H]$^+$.

EXAMPLE 14

Preparation of Ethyl 2-chloro-3-oxo-3-phenylpropanoate

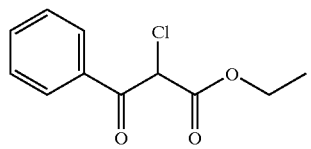

A solution of sulfuryl chloride (12.4 mmol) in toluene (5 mL) was added dropwise via an additional funnel to a solution of ethyl isobutyrylacetate (12.4 mmol) in toluene (20 mL) over 5 minutes at rt. The resulting mixture was stirred at rt overnight. Water was added slowly. The resulting two-phase mixture was basified with saturated NaHCO$_3$ and extracted with EtOAc. The combined organic extracts were washed with brine, dried over anhyd. sodium sulfate, and removed in vacuo to afford 2.2 g (84%) of product as a pale yellow oil. MH$^+$=227.0, retention time (LC-MS)=2.77 min.

EXAMPLE 15

Preparation of Ethyl 2-chloro-4-methyl-3-oxopentanoate

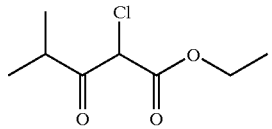

Utilizing the method described for Example 14, the product was obtained in 67% yield (crude). MH$^+$=193.0, retention time (LC-MS)=2.45 min.

EXAMPLE 16

Preparation of Methyl 2-amino-5-phenyl-1,3-thiazole-4-carboxylate

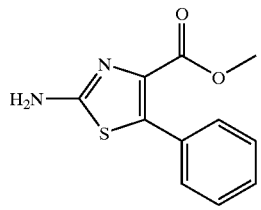

A solution of NaOMe (25 wt %) in MeOH (13.4 mmol) was added to a solution of methyl dichloroacetate (13.4 mmol) and benzaldehyde (14. 8 mmol, 1.1 eq) in Et$_2$O (8 mL) dropwise at 0° C. The reaction mixture was stirred at 0° C. for 1 hour before Et$_2$O and brine were added. The organic layer was separated, dried over anhyd. sodium sulfate, and solvent was removed in vacuo to give a crude material which was dissolved in MeOH (16 mL) containing thiourea (11.4 mmol, 0.85 eq). The resulting reaction mixture was heated to reflux for 18 hours. The crude product mixture was concentrated in vacuo, neutralized with 18M—NH$_4$OH at which time the product precipitated as a white solid. The product was washed with CH$_2$Cl$_2$ (2×), water, and was collected by filtration to afford 1.88 g (70%) of product. MH$^+$=235.1, R$_f$=0.18 (hexanes:EtOAc=1:1), retention time (LC-MS)=1.86 min.

EXAMPLE 17

Preparation of Methyl 2-amino-5-isopropyl-1,3-thiazole-4-carboxylate

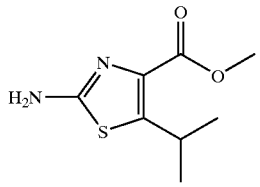

The title compound was prepared according to method of Example 16 in 88% yield. MH$^+$=201.0, retention time (LC-MS)=1.48 min.

EXAMPLE 18

Preparation of Ethyl 2-amino-4-phenyl-1,3-thiazole-5-carboxylate

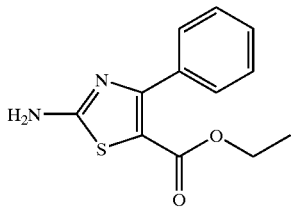

A solution of ethyl 2-chloro-3-oxo-3-phenylpropanoate (9.73 mmol) and thiourea (9.73 mmol) in EtOH (25 mL) was heated at reflux overnight. The resulting mixture was concentrated in vacuo, neutralized with 18M—NH$_4$OH, and extracted with CH$_2$Cl$_2$. The organic phase was washed with brine, dried over anhyd. sodium sulfate, and concentrated to afford a yellow solid that was washed with MeOH (3 mL) and dried to afford the product in 89% yield as a pale yellow solid. MH$^+$=249.1, R$_f$=0.29 (hexanes:EtOAc=1:1). MH$^+$=249.1, retention time (LC-MS)=2.37 min.

EXAMPLE 19

Preparation of Ethyl 2-amino-4-isopropyl-1,3-thiazole-5-carboxylate

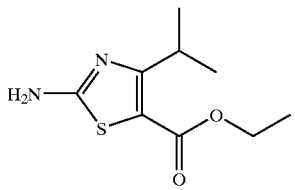

The title compound was prepared according to the method of Example 18 in 65% yield. MH$^+$=215.1, R$_f$=0.66 (hexanes:EtOAc=1:1), retention time (LC-MS)=1.98 min.

EXAMPLE 20

Preparation of Ethyl 5-phenyl-1,3-oxazole-4-carboxylate

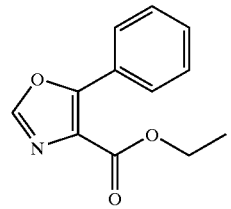

To a mixture of ethyl isocyanoacetate (8.74 mmol) and 1,8-diazabicyclo (5.4.0)undec-7-ene (8.84 mmol) in THF (12 mL) was added a solution of benzoic anhydride (8.84 mmol) in THF (2 mL) at 10° C. with stirring. The resulting mixture was maintained with vigorous stirring for 18 hours at rt. The solvent was removed in vacuo to afford a residue that was partitioned between EtOAc and water. The organic extract was dried over anhyd. sodium sulfate and concentrated to afford a amber oil which was purified by medium pressure column chromatography (Biotage 40S normal phase silica gel column, hexanes:EtOAc=6:1 to 4:1 to 2:1). The product was obtained as a clear oil in 42%. MH$^+$=218.1, retention time (LC-MS)=2.52 min.

EXAMPLE 21

Preparation of Methyl 2-bromo-5-phenyl-1,3-thiazole-4-carboxylate

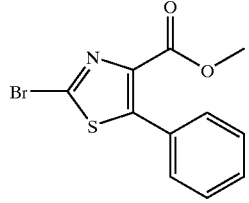

To a dark brown solution of copper(II) bromide (3.85 mmol, 3 eq.) in acetonitrile (5 mL) in a two-neck round-bottomed flask equipped with a condenser was added tert-butyl nitrite (1.92 mmol, 1.5 eq.) slowly at rt. The resulting mixture was heated to 60° C. at which time a suspension of methyl 2-amino-5-phenyl-1,3-thiazole-4-carboxylate (Example 16, 1.28 mmol) in acetonitrile (7 mL) was added dropwise. The resulting reaction mixture was heated at 60° C. for 3 hours, allowed to cool to rt, poured onto 20 mL of 1 M NaOH and extracted with EtOAc. The organic extracts were dried over anhyd. sodium sulfate, concentrated, and purified by medium pressure column chromatography (Biotage 40S normal phase silica gel column, hexanes:EtOAc=5:1). The product was obtained was a pale yellow oil in 88%. MH$^+$=298.0, R$_f$=0.74 (hexanes:EtOAc=2:1), retention time (LC-MS)=3.01 min.

EXAMPLES 22–24

Preparation of Methyl 2-bromo-5-isopropyl-1,3-thiazole-4-carboxylate, Ethyl 2-bromo-4-phenyl-1,3-thiazole-5-carboxylate, and Ethyl 2-bromo-4-isopropyl-1,3-thiazole-5-carboxylate Using essentially the same procedure as Example 21 and substituting the appropriate starting amino compound, the following bromothiazoles were prepared and characterized:

TABLE 2

| Ex. No. | Structure | MS [M + H⁺] | Starting Material (Ex. No.) | Rf | RT (min, LC-MS) |
|---|---|---|---|---|---|
| 22 | 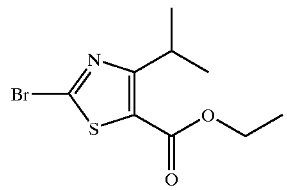 | 264.0 | 18 | 0.51 hexanes: EtOAc 6:1 | 2.83 |
| 23 | 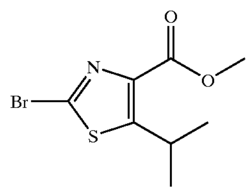 | 312.1 | 16 | 0.65 hexanes: EtOAc 6:1 | 3.46 |
| 24 | 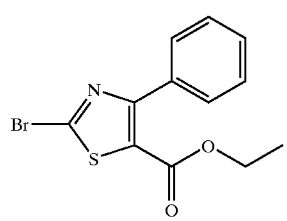 | 278.2 | 17 | 0.74 hexanes: EtOAc 6:1 | 3.54 |

EXAMPLE 25

Preparation of Ethyl 2-iodo-5-phenyl-1,3-oxazole-4-carboxylate

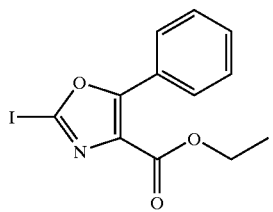

To a solution of ethyl 5-phenyl-1,3-oxazole-4-carboxylate (Example 20, 0.921 mmol, 1 eq.) in THF (7 mL) at −78° C. was added a solution of lithium (trimethylsilyl) amide in THF (1 M in THF, 1.11 mmol, 1.2 eq.) dropwise by syringe. The resulting solution was stirred at −78° C. for 1 hour at which time a solution of iodine (1.38 mmol, 1.5 eq. in 2 mL THF) was added dropwise by a syringe. The reaction mixture was allowed to warm to rt and stirred at this temperature for 1.5 hours. The resulting solution was poured onto 10% aqueous $NaS_2O_3$ (15 mL) and extracted with EtOAc. The organic extracts were washed with brine, dried over anhyd. sodium sulfate, concentrated in vacuo, and purified by medium pressure column chromatography (Biotage 40S normal phase silica gel column, hexanes:EtOAc=9:1). The product was obtained as a pale yellow solid in 82% yield. MH⁺=344.0, $R_f$=0.31 (hexanes:EtOAc=6:1), retention time (LC-MS)=3.01 min.

An embodiment of the present invention is the administration of the compounds of this invention to a human or animal for the treatment of beta-3 adrenergic receptor-mediated conditions such as diabetes, obesity, gastrointestinal disorders including irritable bowel syndrome and intestinal hypermotility disorders, peptic ulcerations, esophagitis, gastritis, and duodenitis, intestinal ulcerations including inflammatory bowel disease, ulcerative colitis, Crohn's disease and proctitis, and gastrointestinal ulcerations, as well as neurogenetic inflammation such as cough and asthma, and depression. It is also believed that the compounds of this invention are effective in the treatment of hypertriglyceridemia, hypercholesterolemia, conditions related to low or high density lipoprotein levels, artherosclerotic disease, and cardiovascular disease and related conditions. Additionally, it is also believed that the compounds of this invention are effective in the treatment of ocular hypertension and glaucoma, and in the treatment of urinary disorders including pollakiuria and incontinence, as well as in the treatment of prostate disease and as topical anti-inflammatory agents.

Therefore, the compounds of this invention are expected to be valuable as therapeutic agents. An embodiment of this invention includes a method of treating beta-3 adrenergic receptor-mediated conditions in a mammal which comprises administering to said mammal a composition containing an amount of the compound of Formula I that is effective in treating the target condition.

The specificity of the compounds of this invention as beta-3 adrenergic receptor agonists can readily be determined by evaluating the affinity of the compound for the different beta adrenergic receptor subtypes and comparing the activity with various receptor subtypes affinities to discover specificity as well as activity. This can be determined by standard and well-known procedures. Such a procedure is described in more detail in the specific experimental example below.

Biological Evaluation of Compounds

The utility of the compounds may be demonstrated by the following procedure. Chinese hamster ovary (CHO) cells that stably express full-length human beta-3-adrenergic receptor (Granneman et al., Mol. Pharmacol. 44:264–270, 1993) may be used in the following procedure. The cell line is grown in 90% F12 nutrient mixture (HAM), 10% fetal bovine serum, 100 units/ml penicillin G sodium, 100 mg/ml streptomycin sulfate, and 2 mM L-glutamine at 37° C. in 95% air and 5% $CO_2$. The transfected cell line is maintained with G-418 (800 μg/ml).

To test the agonist activity, cells are exposed to test compound and then assayed for cAMP production. CHO cells (100 μl) are plated at $5\times10^4$ cells/well of a 96-well plate (Costar, Cambridge, Mass.) to achieve 70% confluency the next day. After overnight incubation at 37° C., media is removed and the cells are treated for 30 minutes at 37° C. with KRP buffer (120 mM NaCl, 5.1 mM KCl, 0.6 mM $MgSO_4 \cdot 7H_2O$, 0.8 mM $CaCl_2 \cdot H_2O$, 12.5 μM Phosphate buffer, 20 μM Hepes pH 7.4)+0.2 μM IBMX (100 μM/well), +1% DMSO, +/− test compounds (10 μM DMSO stocks). Test compounds are assayed from 10 μM to 3 nM with 3-fold serial dilutions. The control agonist, isoproterenol (10 mM stock in 1.1 mM ascorbate), is assayed by 3-fold dilution beginning at 1 μM. After a 30-minute incubation with the test compounds, the buffer/compound mixture is removed. The cells are lysed and cAMP levels are measured using the cAMP SPA screening assay system (Amersham, Arlington Heights, Ill.). The cAMP values are then plotted to ascertain the $EC_{50}$ of each compound tested.

In tests utilizing the above described procedure, the compounds of the present invention were found to have beta-3 adrenergic agonist activity.

Beta-3 adrenergic receptor agonists may be useful for correcting the insulin resistance that underlies two prediabetic states, impaired glucose tolerance (Harris, Diabetes Care 12:464–474, 1989) and impaired fasting glucose (Weyer et al., Diabetes 48:2197–2203, 1999). The ability of a beta-3 adrenergic receptor agonist to restore insulin sensitivity has been demonstrated in a diabetic animal model with marked insulin resistance. Treatment of KK-Ay/Ta diabetic obese mice with a beta-3 adrenergic agonist resulted in marked improvement in the animals' response to insulin (Kato et al., Diabetes 50:113–122, 2001). Insulin resistance in human subjects with impaired glucose tolerance has been treated by troglitazone, another class of insulin sensitizers (Saltiel et al., Diabetes 45:1661–1669, 1996; Saleh et al., Diabetes Rev. 7:55–76, 1999). In such studies, improvement in the insulin responses of these subjects were demonstrated. These overall findings support treating the insulin resistance in prediabetic conditions with insulin sensitizers, including beta-3 adrenergic receptor agonists, to delay or prevent the onset of Type 2 diabetes.

Pharmaceutical Compositions

Based on the above tests, or other well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention or a pharmaceutically acceptable salt thereof may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a pharmaceutically effective amount of a compound identified by the methods described herein, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds identified by the methods described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin,, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly (ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC—CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds identified by the methods described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds identified by the methods described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000)

The following examples are presented to illustrate the invention described herein, but should not be construed as limiting the scope of the invention in any way.

| Capsule Formulation | |
|---|---|
| A capsule formula is prepared from: | |
| Compound of this invention | 40 mg |
| Starch | 109 mg |
| Magnesium stearate | 1 mg |

The components are blended, passed through an appropriate mesh sieve, and filled into hard gelatin capsules.

| Tablet Formulation | |
|---|---|
| A tablet is prepared from: | |
| Compound of this invention | 25 mg |
| Cellulose, microcrystaline | 200 mg |
| Colloidal silicon dioxide | 10 mg |
| Stearic acid | 5.0 mg |

The ingredients are mixed and compressed to form tablets. Appropriate aqueous and non-aqueous coatings may be applied to increase palatability, improve elegance and stability or delay absorption.

Sterile IV Solution

A 5 mg/ml solution of the desired compound of this invention is made using sterile, injectable water, and the pH is adjusted if necessary. The solution is diluted for administration to 1–2 mg/ml with sterile 5% dextrose and is administered as an IV infusion over 60 minutes.

Intramuscular suspension

The following intramuscular suspension is prepared:

| Compound of this invention | 50 mg/ml |
|---|---|
| Sodium carboxymethylcellulose | 5 mg/ml |
| TWEEN 80 | 4 mg/ml |
| Sodium chloride | 9 mg/ml |
| Benzyl alcohol | 9 mg/ml |

The suspension is administered intramuscularly.

Hard Shell Capsules

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

It should be apparent to one of ordinary skill in the art that changes and modifications can be made to this invention without departing from the spirit or scope of the invention as it is set forth herein.

We claim:

1. A compound of Formula 1:

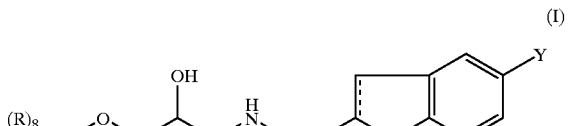

(I)

wherein

--- represents a single or double bond;

R is hydroxy, oxo, halo, cyano, nitro, $C_1$–$C_{10}$ alkyl, $C_1$–$C_{10}$ haloalkyl, $CF_3$, $NR^1R^1$, $SR^1$, $OR^1$, $SO_2R^2$, $OCOR^2$, $NR^1COR^2$, $COR^2$, $NR^1SO_2R^2$, phenyl, or a 5- or 6-membered heterocyclic ring having 1 to 4 heteroatoms selected from O, S, and N, wherein said phenyl or 5- or 6-membered heterocyclic ring moiety being optionally substituted with one or more substituents independently selected from hydroxy, $R^1$, halo, cyano, $NR^1R^1$, $SR^1$, $CF_3$, $OR^1$, $C_3$–$C_8$ cycloalkyl, $NR^1COR^2$, $COR^2$, $SO_2R^2$, $OCOR^2$, $NR^1SO_2R^2$, $C_1$–$C_{10}$ alkyl, and $C_1$–$C_{10}$ alkoxy;

$R^1$ is hydrogen or $C_1$–$C_{10}$ alkyl optionally substituted with 1 to 4 substituents each independently selected from hydroxy, halo, $CO_2H$, $CO_2(C_1$–$C_{10}$ alkyl), $C_1$–$C_{10}$ alkoxy, and phenyl optionally substituted with $CO_2H$, $CO_2(C_1$–$C_{10}$ alkyl) or $C_1$–$C_{10}$ alkyl; or $C_3$–$C_8$ cycloalkyl, phenyl or naphthyl, each optionally substituted with 1 to 4 substituents each independently selected from halo, nitro, oxo, $C_1$–$C_{10}$ alkyl, $C_1$–$C_{10}$ alkoxy, and $C_1$–$C_{10}$ alkylthio;

$R^2$ is $R^1$, $OR^1$, $NR^1R^1$ or a 5- or 6-membered heterocyclic ring with one or more heteroatoms selected from O, S, and N, said heterocyclic ring being optionally substituted with C1–$C_{10}$ alkyl optionally substituted with 1 to 4 substituents each independently selected from hydroxy, halo, $CO_2H$, $CO_2$($C_1$–$C_{10}$ alkyl), $C_1$–$C_{10}$ alkoxy, and phenyl optionally substituted with $CO_2H$, $CO_2$($C_1$–$C_{10}$ alkyl) or $C_1$–$C_{10}$ alkyl; or $C_3$–$C_8$ cycloalkyl, phenyl or naphthyl, each optionally substituted with 1 to 4 substituents each independently selected from halo, nitro, oxo, $C_1$–$C_{10}$ alkyl, $C_1$–$C_{10}$ alkoxy, and $C_1$–$C_{10}$ alkylthio;

Ar is phenyl optionally fused to a 5- or 6-membered heterocyclic ring having 1 to 4 heteroatoms each independently selected from O, S, and N, wherein the heterocyclic ring in turn is optionally fused to another phenyl ring; or a 5-or 6-membered heterocyclic ring having 1 to 4 heteroatoms each independently selected from N, S, and O;

Y is $C_1$–$C_{10}$ alkyl optionally substituted with 1 to 4 substituents each independently selected from hydroxy, halo, $CO_2H$, $CO_2$($C_1$–$C_{10}$ alkyl), $C_1$–$C_{10}$ alkoxy, $C_1$–$C_{10}$ alkylthio, and phenyl optionally substituted with $CO_2H$, $CO_2$($C_1$–$C_{10}$ alkyl), or $C_1$–$C_{10}$ alkyl; or phenyl optionally fused to another phenyl ring or to a 5- or 6-membered heterocyclic ring having 1 to 4 heteroatoms selected from N, S, and O; or a 5- or 6-membered heterocyclic ring having one or more heteroatoms selected from N, S, and O, optionally fused to a phenyl ring;

wherein said phenyl or 5- or 6-membered heterocyclic ring moiety being optionally substituted with one or more substituents independently selected from $COR^2$, halo, $NO_2$, $OR^1$, $R^1$, $SR^1$, $NR^1R^1$, ($C_1$–$C_{10}$ alkyl) $OR^2$, phenyl or tetrazolo;

a is 0, 1, 2, 3, 4, or 5; and d is 1 or 2;

and pharmaceutically acceptable salts or esters thereof.

2. The compound of claim 1, wherein

Y is phenyl or a 5- or 6-membered heterocyclic ring having one or more heteroatoms selected from N, S, and O, wherein said phenyl or 5- or 6-membered heterocyclic ring moiety being optionally substituted with one or more substituents independently selected from $COR^2$, halo, $NO_2$, $OR^1$, $R^1$, $SR^1$, $NR^1R^1$, ($C_1$–$C_{10}$ alkyl) $OR^2$, phenyl or tetrazolo; and R, $R^1$, $R^2$, Ar, a, and d are as defined in claim 1.

3. The compound of claim 1, wherein

Y is $C_1$–$C_{10}$ alkyl optionally substituted with 1 to 4 substituents each independently selected from hydroxy, halo, $CO_2H$, $CO_2$/($C_1$–$C_{10}$ alkyl), $C_1$–$C_{10}$ alkoxy, $C_1$–$C_{10}$ alkylthio, and phenyl optionally substituted with $CO_2H$, $CO_2$($C_1$–$C_{10}$ alkyl), or $C_1$–$C_{10}$ alkyl; and R, $R^1$, $R^2$, Ar, a, and d are as defined in claim 1.

4. The compound of claim 1, wherein $R^2$ is $OR^1$;

Ar is phenyl optionally fused to a 5- or 6-membered heterocyclic ring having 1 to 4 heteroatoms each independently selected from O, S, and N, or a 5- or 6-membered heterocyclic ring having 1 heteroatom selected from N, S, and O;

Y is phenyl substituted with $COR^2$;

a is 0, 1, or 2;

d is 1;

and R and $R^1$ are as defined in claim 1.

5. The compound of claim 1, wherein

Ar is a 5- or 6-membered heterocyclic ring having 1 heteroatom selected from N, S, and O;

a is 0; and

R, $R^1$, $R^2$, Y, and d are as defined in claim 1.

6. A method of treating a beta-3 adrenergic receptor-mediated condition comprising the step of administering to a patient in need thereof a pharmaceutically effective amount of a compound of claim 1.

7. A method of treating obesity comprising the step of administering to a patient in need thereof a pharmaceutically effective amount of a compound of claim 1.

8. A method of treating diabetes comprising the step of administering to a patient in need thereof a pharmaceutically effective amount of a compound of claim 1.

9. A method of treating a patient with impaired fasting glucose or impaired glucose tolerance comprising the step of administering to said patient in need thereof a pharmaceutically effective amount of a compound of claim 1.

10. A method of treating gastrointestinal disorders comprising the step of administering to a patient in need thereof a pharmaceutically effective amount of a compound of claim 1.

11. A method of treating hypertriglyceridemia, hypercholesteolemia, artherosclerotic disorders, or cardiovascular disorders comprising the step of administering to a patient in need thereof a pharmaceutically effective amount of a compound of claim 1.

12. A method for lowering high-density lipoprotein levels comprising the step of administering to a patient in need thereof a pharmaceutically effective amount of a compound of claim 1.

13. A method of treating urinary disorders comprising the step of administering to a patient in need thereof a pharmaceutically effective amount of a compound of claim 1.

14. A method of claim 13, wherein said urinary disorders is selected from the group consisting of pollakiuria and incontinence.

15. A pharmaceutical composition comprising an effective amount of a compound of claim 1 or a pharmaceutically acceptable salt or ester thereof and a pharmaceutically acceptable carrier.

16. A composition comprising an effective amount of a compound of claim 1 or a salt or ester thereof and an inert carrier.

* * * * *